United States Patent
Laufer et al.

(10) Patent No.: US 10,446,013 B2
(45) Date of Patent: *Oct. 15, 2019

(54) PERSONNEL PROXIMITY DETECTION AND TRACKING SYSTEM

(71) Applicant: OSLA Technologies, LLC, Alpharetta, GA (US)

(72) Inventors: Zohar Laufer, Johns Creek, GA (US); Charles Agnew Osborne, Jr., Cumming, GA (US)

(73) Assignee: Valve Solutions, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/979,360

(22) Filed: May 14, 2018

(65) Prior Publication Data

US 2018/0315293 A1    Nov. 1, 2018

Related U.S. Application Data

(63) Continuation of application No. 15/674,957, filed on Aug. 11, 2017, now Pat. No. 9,972,193, which is a (Continued)

(51) Int. Cl.
  *G08B 23/00*     (2006.01)
  *G08B 21/24*     (2006.01)
  *H04W 4/02*      (2018.01)

(52) U.S. Cl.
  CPC ............ *G08B 21/245* (2013.01); *H04W 4/02* (2013.01)

(58) Field of Classification Search
  None
  See application file for complete search history.

(56) References Cited

U.S. PATENT DOCUMENTS

| | | |
|---|---|---|
| 5,610,589 A | 3/1997 | Evans et al. |
| 5,808,553 A | 9/1998 | Cunningham |

(Continued)

FOREIGN PATENT DOCUMENTS

| | | |
|---|---|---|
| WO | WO2004/086287 A2 | 10/2004 |
| WO | WO2010/099488 A1 | 9/2010 |

OTHER PUBLICATIONS

International Search Report and Written Opinion for related application, PCT/US2015/038996, dated Oct. 28, 2015.

(Continued)

*Primary Examiner* — Adolf Dsouza
(74) *Attorney, Agent, or Firm* — Womble Bond Dickinson (US) LLP

(57) ABSTRACT

Systems and methods for tracking, locating, identifying, or mapping movements of persons or personnel within a facility may include badges carried by selected persons or personnel through the facility, and these badges can each include a transmitter configured to transmit a series of signals including signature information identifying the badges and also identifying codes of each signal transmitted. In addition, a series of receivers can be positioned at selected locations of the facility and can receive the signals transmitted by the transmitters of the badges, and these receivers can be configured to identify each badge from which signals are received based upon signature information for identified badges and also to determine the proximity, range, distance, or zone between the badge identified and one or more receivers.

21 Claims, 17 Drawing Sheets

Related U.S. Application Data continuation of application No. 14/790,473, filed on Jul. 2, 2015, now Pat. No. 9,741,233.

(60) Provisional application No. 62/020,728, filed on Jul. 3, 2014.

(56) References Cited

U.S. PATENT DOCUMENTS

| | | |
|---|---|---|
| 5,864,894 A | 2/1999 | Fedele |
| 5,900,801 A | 5/1999 | Heagle et al. |
| 5,939,974 A | 8/1999 | Heagle et al. |
| 5,945,910 A | 8/1999 | Gorra |
| 6,147,607 A | 11/2000 | Lynn |
| 6,236,317 B1 | 5/2001 | Cohen et al. |
| 6,236,953 B1 | 5/2001 | Segal |
| 6,278,372 B1 | 8/2001 | Velasco et al. |
| 6,346,886 B1 | 2/2002 | DeLaHuerga |
| 6,347,414 B2 | 2/2002 | Contadini et al. |
| 6,645,435 B2 | 11/2003 | Dawson et al. |
| 6,882,278 B2 | 4/2005 | Winings et al. |
| 6,883,563 B2 | 4/2005 | Smith |
| 6,975,231 B2 | 12/2005 | Lane et al. |
| 7,242,307 B1 | 7/2007 | LeBlond et al. |
| 7,271,719 B2 | 9/2007 | Ku et al. |
| 7,271,728 B2 | 9/2007 | Taylor et al. |
| 7,293,645 B2 | 11/2007 | Harper et al. |
| 7,315,245 B2 | 1/2008 | Lynn et al. |
| 7,372,367 B2 | 5/2008 | Lane et al. |
| 7,375,640 B1 | 5/2008 | Plost |
| 7,408,470 B2 | 8/2008 | Wildman et al. |
| 7,423,533 B1 | 9/2008 | LeBlond et al. |
| 7,425,900 B2 | 9/2008 | Lynn et al. |
| 7,477,148 B2 | 1/2009 | Lynn et al. |
| 7,598,854 B2 | 10/2009 | Wong |
| 7,659,824 B2 | 2/2010 | Prodanovich et al. |
| 7,755,494 B2 | 7/2010 | Melker et al. |
| 7,770,782 B2 | 8/2010 | Sahud |
| 7,779,059 B2 | 8/2010 | Bourland et al. |
| 7,782,214 B1 | 8/2010 | Lynn |
| 7,812,730 B2 | 10/2010 | Wildman et al. |
| 7,818,083 B2 | 10/2010 | Glenn et al. |
| 7,825,812 B2 | 11/2010 | Ogrin et al. |
| 7,855,651 B2 | 12/2010 | LeBlond et al. |
| 7,893,842 B2 | 2/2011 | Deutsch |
| 7,898,407 B2 | 3/2011 | Hufton et al. |
| 7,952,484 B2 | 5/2011 | Lynn |
| 7,978,083 B2 | 7/2011 | Melker et al. |
| 8,085,155 B2 | 12/2011 | Prodanovich et al. |
| 8,094,029 B2 | 1/2012 | Ortiz et al. |
| 8,146,613 B2 | 4/2012 | Barnhill et al. |
| 8,164,439 B2 | 4/2012 | Dempsey et al. |
| 8,169,327 B2 | 5/2012 | Lynn |
| 8,196,810 B2 | 6/2012 | Sahud |
| 8,212,653 B1 | 7/2012 | Goldstein et al. |
| 8,229,185 B2 | 7/2012 | Ennis et al. |
| 8,237,558 B2 | 8/2012 | Seyed Momen et al. |
| 8,249,295 B2 | 8/2012 | Johnson |
| 8,250,657 B1 | 8/2012 | Nachenberg et al. |
| 8,264,343 B2 | 9/2012 | Snodgrass |
| 8,294,584 B2 | 10/2012 | Plost |
| 8,294,585 B2 | 10/2012 | Barnhill |
| 8,299,896 B2 | 10/2012 | Mahmoodi et al. |
| 8,334,777 B2 | 12/2012 | Wilson et al. |
| 8,344,893 B1 | 1/2013 | Drammeh |
| 8,350,706 B2 | 1/2013 | Wegelin et al. |
| 8,368,544 B2 | 2/2013 | Wildman et al. |
| 8,377,229 B2 | 2/2013 | Barnhill et al. |
| 8,395,515 B2 | 3/2013 | Tokhtuev et al. |
| 8,400,309 B2 | 3/2013 | Glenn et al. |
| 8,405,503 B2 | 3/2013 | Wong |
| 8,427,323 B2 | 4/2013 | Alper et al. |
| 8,448,848 B2 | 5/2013 | Sahud |
| 8,482,406 B2 | 7/2013 | Snograss |
| 8,498,851 B2 | 7/2013 | Ehrnsperger et al. |
| 8,502,680 B2 | 8/2013 | Tokhtuev et al. |
| 8,502,681 B2 | 8/2013 | Bolling et al. |
| 8,525,666 B2 | 9/2013 | Melker et al. |
| 8,547,220 B1 | 10/2013 | Dempsey et al. |
| 8,558,660 B2 | 10/2013 | Nix et al. |
| 8,558,701 B2 | 10/2013 | Wegelin et al. |
| 8,564,431 B2 | 10/2013 | Snodgrass |
| 8,566,478 B2 | 10/2013 | Ota et al. |
| 8,566,932 B1 | 10/2013 | Hotta et al. |
| 8,587,437 B2 | 11/2013 | Kyle et al. |
| 8,598,996 B2 | 12/2013 | Wildman et al. |
| 8,633,816 B2 | 1/2014 | Snodgrass et al. |
| 8,640,275 B2 | 2/2014 | Lawson et al. |
| 8,673,210 B2 | 3/2014 | Deshays |
| 8,674,840 B2 | 3/2014 | Snodgrass |
| 8,698,637 B2 | 4/2014 | Raichman |
| 8,717,177 B2 | 5/2014 | Cartner |
| 8,742,932 B2 | 6/2014 | Casares |
| 8,744,623 B2 | 6/2014 | Drake et al. |
| 8,746,558 B2 | 6/2014 | Healy et al. |
| 9,741,233 B2 | 8/2017 | Laufer et al. |
| 9,972,193 B2 | 5/2018 | Laufer et al. |
| 2002/0135486 A1 | 9/2002 | Brohagen et al. |
| 2003/0019536 A1 | 1/2003 | Smith |
| 2005/0231373 A1 | 10/2005 | Lynn et al. |
| 2007/0020212 A1 | 1/2007 | Bernal et al. |
| 2007/0096930 A1 | 5/2007 | Cardoso |
| 2007/0229288 A1 | 10/2007 | Ogrin et al. |
| 2007/0247316 A1 | 10/2007 | Wildman et al. |
| 2008/0001763 A1 | 1/2008 | Raja et al. |
| 2008/0087719 A1 | 4/2008 | Sahud |
| 2008/0100441 A1 | 5/2008 | Prodanovich et al. |
| 2008/0126126 A1 | 5/2008 | Ballai |
| 2008/0136649 A1 | 6/2008 | Van De Hey |
| 2008/0303658 A1 | 12/2008 | Melker et al. |
| 2009/0091458 A1 | 4/2009 | Deutsch |
| 2009/0189759 A1 | 7/2009 | Wildman et al. |
| 2009/0195385 A1 | 8/2009 | Huang et al. |
| 2009/0224907 A1 | 9/2009 | Sinha et al. |
| 2009/0224924 A1 | 9/2009 | Thorp |
| 2009/0267776 A1 | 10/2009 | Glenn |
| 2009/0272405 A1 | 11/2009 | Barnhill et al. |
| 2009/0273477 A1 | 11/2009 | Barnhill |
| 2010/0073162 A1 | 3/2010 | Johnson et al. |
| 2010/0090837 A1 | 4/2010 | Jung et al. |
| 2010/0094581 A1 | 4/2010 | Cagle |
| 2010/0117823 A1 | 5/2010 | Wholtjen |
| 2010/0155416 A1 | 6/2010 | Johnson |
| 2010/0164728 A1 | 7/2010 | Plost |
| 2010/0231385 A1 | 9/2010 | Melker et al. |
| 2010/0238021 A1 | 9/2010 | Harris |
| 2010/0265059 A1 | 10/2010 | Melker et al. |
| 2010/0328076 A1 | 12/2010 | Kyle et al. |
| 2011/0018998 A1 | 1/2011 | Guzik |
| 2011/0057799 A1 | 3/2011 | Taneff |
| 2011/0121974 A1 | 5/2011 | Tenarvitz et al. |
| 2011/0125524 A1 | 5/2011 | Tenarvitz et al. |
| 2011/0169643 A1 | 7/2011 | Cartner |
| 2011/0169645 A1 | 7/2011 | Cartner et al. |
| 2011/0169646 A1 | 7/2011 | Raichman |
| 2011/0193703 A1 | 8/2011 | Payton et al. |
| 2011/0205061 A1 | 8/2011 | Wilson et al. |
| 2011/0254682 A1 | 10/2011 | Sigrist Christensen |
| 2011/0273298 A1 | 11/2011 | Snodgrass et al. |
| 2011/0291841 A1 | 12/2011 | Hollock et al. |
| 2011/0316695 A1 | 12/2011 | Li et al. |
| 2011/0316701 A1 | 12/2011 | Alper et al. |
| 2011/0316703 A1 | 12/2011 | Butler et al. |
| 2012/0013470 A1 | 1/2012 | Lynn |
| 2012/0055986 A1 | 3/2012 | Sahud |
| 2012/0062382 A1 | 3/2012 | Taneff |
| 2012/0112906 A1 | 5/2012 | Borke et al. |
| 2012/0112914 A1 | 5/2012 | Wegelin et al. |
| 2012/0158419 A1 | 6/2012 | Nuthi |
| 2012/0256742 A1 | 10/2012 | Snodgrass et al. |
| 2012/0268277 A1 | 10/2012 | Best |
| 2012/0270261 A1 | 10/2012 | Mayer et al. |
| 2012/0274468 A1 | 11/2012 | Wegelin et al. |
| 2012/0303159 A1 | 11/2012 | Drake et al. |
| 2013/0025714 A1 | 1/2013 | Hermann |

(56) References Cited

U.S. PATENT DOCUMENTS

| | | |
|---|---|---|
| 2013/0027199 A1 | 1/2013 | Bonner |
| 2013/0033376 A1 | 2/2013 | Seyed Momen et al. |
| 2013/0035900 A1 | 2/2013 | Purcell et al. |
| 2013/0038446 A1* | 2/2013 | Huseth ............... G08B 21/0202 340/539.13 |
| 2013/0045685 A1 | 2/2013 | Kiani |
| 2013/0076514 A1 | 3/2013 | Wegelin et al. |
| 2013/0113619 A1 | 5/2013 | Snodgrass |
| 2013/0120120 A1 | 5/2013 | Long et al. |
| 2013/0187779 A1 | 7/2013 | Pokrajac |
| 2013/0218583 A1 | 8/2013 | Marcolongo et al. |
| 2013/0229276 A1 | 9/2013 | Hunter |
| 2013/0234855 A1 | 9/2013 | Knighton |
| 2013/0257615 A1 | 10/2013 | Iseri et al. |
| 2013/0262034 A1 | 10/2013 | Iseri et al. |
| 2013/0268293 A1 | 10/2013 | Knudson et al. |
| 2013/0291947 A1 | 11/2013 | Chandler et al. |
| 2014/0009292 A1 | 1/2014 | Long et al. |
| 2014/0015670 A1 | 1/2014 | Wegelin et al. |
| 2014/0022073 A1 | 1/2014 | Balinski et al. |
| 2014/0022074 A1 | 1/2014 | Balinski et al. |
| 2014/0035744 A1 | 2/2014 | Wildman et al. |
| 2014/0046722 A1 | 2/2014 | Rosenbloom et al. |
| 2014/0049391 A1 | 2/2014 | Bolling et al. |
| 2014/0104062 A1 | 4/2014 | Weiner |
| 2014/0139339 A1 | 5/2014 | Jones et al. |
| 2014/0167917 A2 | 6/2014 | Wallace et al. |
| 2016/0005300 A1 | 1/2016 | Laufer et al. |
| 2017/0365159 A1 | 12/2017 | Laufer et al. |

OTHER PUBLICATIONS

Extended European Search Report for related European Patent Application, 15815829.5 (PCT/US2015/038996), dated Feb. 5, 2018.

* cited by examiner

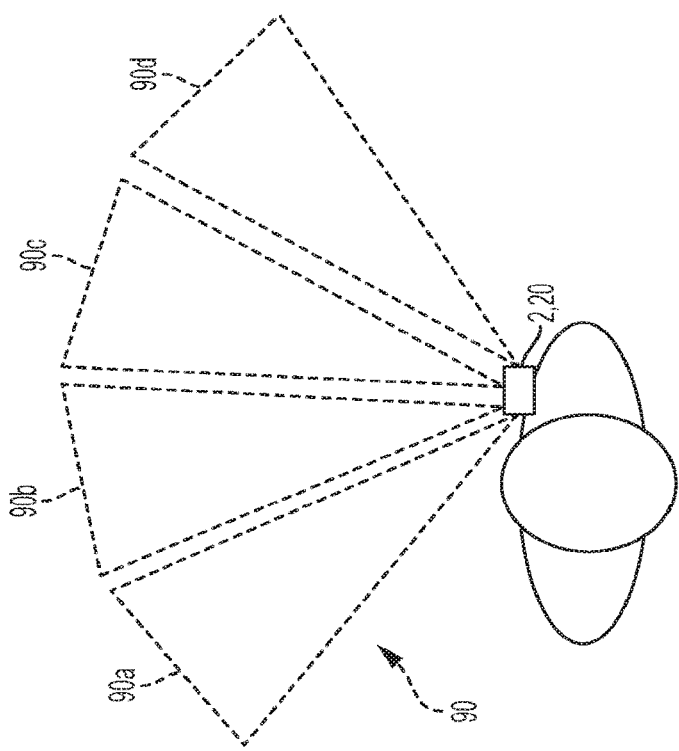
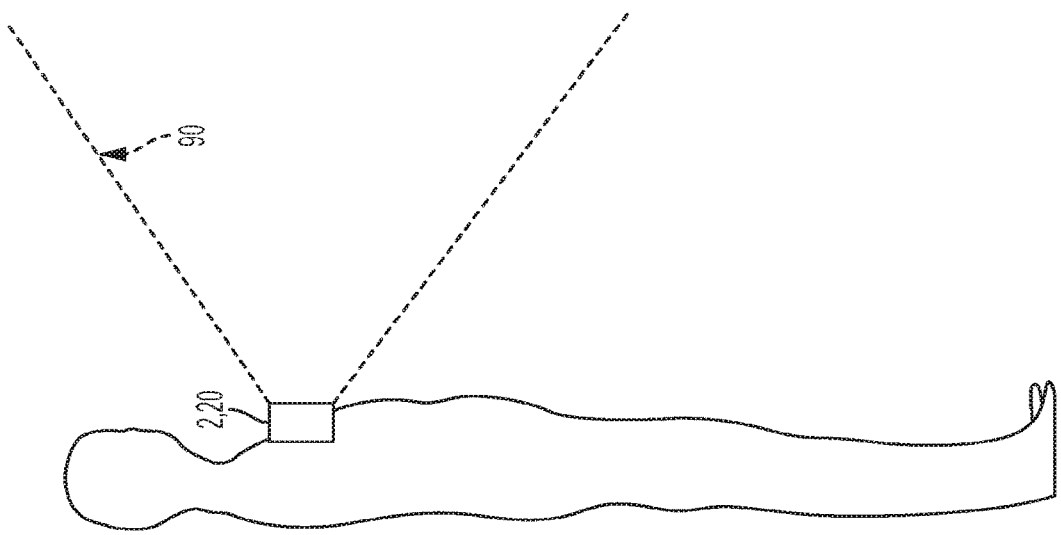
FIG. 7A
FIG. 7B

PERSONNEL PROXIMITY DETECTION AND TRACKING SYSTEM

CROSS REFERENCE TO RELATED APPLICATIONS

The present Patent Application is a continuation of previously filed, U.S. patent application Ser. No. 15/674,957, filed Aug. 11, 2017, which is a continuation of previously filed, U.S. patent application Ser. No. 14/790,473, filed Jul. 2, 2015, which claims the benefit of U.S. Provisional Patent Application No. 62/020,728, filed Jul. 3, 2014.

INCORPORATION BY REFERENCE

The specification and drawings of U.S. patent application Ser. No. 15/674,957, filed Aug. 11, 2017; U.S. patent application Ser. No. 14/790,473, filed Jul. 2, 2015; and U.S. Provisional Patent Application No. 62/020,728, filed Jul. 3, 2014, are specifically incorporated by reference herein as if set forth in their entireties.

TECHNICAL FIELD AND BACKGROUND

In testing of areas of various facilities, such as hospital rooms, researchers have found antibiotic-resistant strains of bacteria on multiple surfaces, including bedrails, supply carts, and floors. Such bacteria have been linked to causing numerous infection outbreaks in health care facilities over the last decade, and can survive on surfaces for long periods of time. One study sampling at least the following surfaces: bedrails, bedside tables, door handles, vital sign monitor touchpads, nurse call buttons, sinks, supply cart drawer handles, infusion pumps, ventilator surface touch pads, and the floor on both sides of the patient's bed, found that, of the surfaces tested, the surfaces most contaminated were supply cart handles, floors, infusion pumps, ventilator touchpads, and bedrails. These findings raise concerns since these contaminated surfaces are touched routinely by medical personnel and may be a source of hospital-based transmission of highly infectious diseases, such as staph, MRSA and other serious infections to patients. Accordingly, to address such concerns, embodiments of the present disclosure generally relate to a proximity detecting and tracking methods and systems for a selected facility, such as a medical facility.

SUMMARY

In one embodiment, the present application can include multi-purpose methods and systems for tracking, identifying, locating, and/or mapping the movements or activities of persons in a selected facility. For example, the systems and methods according to the present disclosure can allow for tracking and mapping of the movements and activities of medical workers or patients in a medical facility using one or more primary transmitters and a series of primary receivers. These tracked movements and activities can further be cross-referenced with health information to allow for real time or forensic mapping of activities in the medical facility or to provide real time instructions to medical personnel.

In an additional embodiment, the present disclosure is generally directed to a compliance system for hospitals to assist in minimizing contaminants transmitted from one patient to another via health care providers. The system can include one or more transmitters and/or receivers incorporated into personal badges and receivers coupled to antibacterial dispensers that can be coded or programmed for identifying, detecting and locating health care providers within a hospital or other selected environment, as well as within identified sub-areas or zones within the selected environment. For example, the healthcare providers can carry badges with a front and one or more side beam transmitters, and which have a rechargeable and/or replaceable power source.

In an even further embodiment, a system and method is provided for tracking and monitoring proximity and/or movement of patient treatment providers and/or other personnel into and within an environment in which there is a risk of exposure to potential contamination, infection, etc., such as a patient room, or other treatment area that may require or necessitate application of sanitizing or disinfecting treatment. This system can be configured to utilize detection of different intensity infra-red (IR) energy bursts emitting from a badge IR beam for communications, mapping of persons or objects carrying the badges, signaling alerts and/or initiating other actions. The badge beams can be provided or emitted at varying intervals or patterns and/or directed or dispersed in a manner so as to be detected by sensors generally located at key or substantially centralized locations, such as on a wall behind a patient bed, or on the bed, and will be generated from a badge carried by a nurse, doctor, staff or other personnel. Such sensors also can be programmed or provided with a prescribed or selected sensitivity level to enable detection of badge IR beams of a certain intensity or within a prescribed proximity or distance. For example, the badge IR beam bursts can be directed or focused in directions at which constant sensitivity sensors will be oriented and/or placed with respect to a doorway or various other objects in a room. Each IR beam or burst can be transmitted sequentially and its intensity can vary incrementally, and further can include a badge signature. The distance from the sensor at which the beam/pulse is translated also can be varied. Information, including badge signature, time, distance to a detecting sensor can be sent wirelessly to a server or central processor, which may be connected to a cloud-based network, along with the recorded sensor and the dispenser's signatures.

The system can use horizontal IR communication between the user badges and other detecting units, such as dispensers and various other mounted and/or stand-alone units at desired location about a facility, and/or other types of communications as needed. For example, RF transmitters can be used to send the collected information wirelessly to a cloud-based network in communication with a central server or processor, for recording and processing to provide desired data reports. The system also can provide devices higher precision in collection of information and tracking of movements of health care providers of other personnel, especially in critical areas around the patient.

In one example embodiment, when a health care provider is entering a patient room and approaching the patient close area, a signal from a sanitizing dispenser can be received by the badge, such that the badge "wakes up," sending its signature back to the dispenser, which can send detection ID and other information to the cloud. The dispenser can then initiate a "wash hands" alert for about 10 seconds and, if activated within the period, send a compliance signal/message. If not activated within the time period, the system can send a non-compliance message.

When the health care provider approaches the patient, their badge side IR transmitter(s) also can communicate with one of a series of fixed or receiving sensors, which can be of a constant or varying sensitivity. These sensors can be mounted to a wall or patient bed, and can receive the signals sent by the badge transmitter(s), such as detect intensity or other variables thereof, for use in defining X and Y locations of the badge with reference to the patient's body, and at a desired/measured time. Such information can be recorded and an alert issued if a non-compliance message was previously entered for the detected/identified badge. Additionally, the sensors can be maintained in a low power or sleep mode until receiving a signal from a badge transmitter or from the sanitizing dispenser.

Thereafter, when the health care giver is approaching the exit door, their badge signal can activate a door/portal or exit unit, which will send activation data back to the dispenser, which, in turn, will send the data to the cloud. The exit unit signal also can cause the dispenser to issue a "wash hands" alert, and further can reset the badge, and potentially the fixed sensor(s) back to a "sleep mode," as needed.

In other embodiments, a proximity warning system further is provided for warning of the proximity of medical personnel within at least one zone of interest adjacent a patient's bed. The personnel proximity warning system includes at least one primary sensor deployed to receive radiation from at least part of the zone of interest. The primary sensor is configured to produce a primary output indicative of a quantity of electromagnetic radiation incident on the primary sensor. At least one transmitter is configured to transmit an electromagnetic signal toward at least part of the zone of interest. A processing module is associated with at least the primary sensor and is responsive to the primary output to generate a warning signal to alert personnel of the need to wash and/or sanitize their hands before coming into contact with a patient. The transmitted electromagnetic signal generally can lie within the infrared portion of the electromagnetic spectrum. A signal generator will be associated with the at least one transmitter and can be configured to generate an underlying pulsed power supply. For example, the power supply can have a duty cycle of less than about five (5) %.

In some embodiments, a modulator module could be associated with at least one transmitter element of a primary transmission device and configured to modulate the transmission power of the electromagnetic signal cyclically between at least two relative power levels corresponding to at least two different-sized zones of interest, a higher one of the at least two relative power levels being generated for less than about 20% of each cycle.

There also can be provided, according to the teachings of the present disclosure, a proximity warning system for warning of the proximity of an obstacle within a zone of interest, the zone being delineated at least in part by a virtual line, the system comprising: (a) a plurality of transmitter elements responsive to an actuating power supply to transmit an electromagnetic signal generally towards the virtual line; and (b) at least one sensor responsive to a received reflected electromagnetic signal generally from along the virtual line to generate a reception signal. The configuration and the deployment of the transmitter elements and of the at least one sensor further generally will be selected such that, for a given level of actuating power supply, the reception signal resulting from reflection of the transmitted electromagnetic signal from the surface of an object remains substantially constant as the object is moved along a path approximately corresponding to a part of the virtual line.

According to a further feature of the present disclosure, each of the transmitter elements can have a transmission intensity that decreases as a function of angle from a maximum intensity direction. In addition, two or more of the transmitter elements can be deployed to facilitate a maximum intensity transmission in angularly spaced directions, such that a total transmitted intensity assumes a minimum value at an intermediate angular position. The sensor also can have a reception sensitivity which decreases as a function of angle from a maximum sensitivity direction, the sensor being aligned with its maximum sensitivity direction aligned substantially with the intermediate angular position of minimum total transmitted intensity.

According to yet another feature of the present disclosure, each of the transmitter elements has a transmission intensity which decreases as a function of angle from a maximum intensity direction to a 50% transmission intensity direction, two of the transmitter elements being deployed with their maximum intensity directions angularly spaced such their 50% transmission intensity directions are substantially aligned.

According to still a further feature of the present disclosure, there also can be provided a transmission power modifier associated with each of the transmitter elements, each of the transmission power modifiers modifying the effect of the actuating power supply upon the corresponding one of the transmitter elements such that a combined intensity of the electromagnetic signal from all of the transmitter elements reaching the part of the virtual line can be substantially constant along the line.

In another embodiment, the present disclosure can provide an infrared identification tracking method and system for hospitals and/or food processing hygiene compliance. In this embodiment, each healthcare person wears a badge on their chest. The badge can comprise, for example, at least three infrared LED's, for example, arranged in a configuration with one LED in the front and one LED on each side, and will provide a coded person's identification and position within a predetermined zone. Other configurations also can be used. The predetermined zone can be designated by several factors, such as, distance, front, right, left side seen from the orientation of the badge. The badge can also include at least one infrared receiver that functions to "wake up" the badge when the badge receives a signal from a dispenser or other tracking unit, such as those that are installed within a facility. Generally, the badge is in a ready state and can be woken up in order to provide for battery saving.

These and other advantages and aspects of the embodiments of the disclosure will become apparent and more readily appreciated from the following detailed description of the embodiments taken in conjunction with the accompanying drawings, as follows.

BRIEF DESCRIPTION OF THE DRAWINGS

FIG. 7A illustrates a top view of a primary transmitter showing infrared badge subzones worn by such personnel according to one aspect of the present disclosure.

FIG. 7B is a side view of primary transmitter shown in FIG. 7A.

Those skilled in the art will appreciate and understand that, according to common practice, the various features of the drawings discussed below are not necessarily drawn to scale, and that the dimensions of various features and elements of the drawings may be expanded or reduced to more clearly illustrate the embodiments of the present invention described herein.

DETAILED DESCRIPTION

The following detailed description is provided as an enabling teaching of embodiments of the invention. Those skilled in the relevant art will recognize that many changes can be made to the embodiments described, while still obtaining the beneficial results. It will also be apparent that some of the desired benefits of the embodiments described can be obtained by selecting some of the features of the embodiments without utilizing other features. Accordingly, those who work in the art will recognize that many modifications and adaptations to the embodiments described are possible and may even be desirable in certain circumstances. Thus, the following description is provided as illustrative of the principles of the invention and not in limitation thereof, since the scope of the invention is defined by the claims.

In general, embodiments of the present application can include multi-purpose methods and systems for tracking, identifying, locating, and/or mapping the movements or activities of persons, e.g., health care facility employees and patients, restaurant employees, factory workers, or laboratory personnel, in a selected facility, e.g., medical facilities, restaurants, factories, manufacturing facilities, or laboratories, and their specific activities, such as providing patient care or complying with sanitation requirements.

Figure 1A:
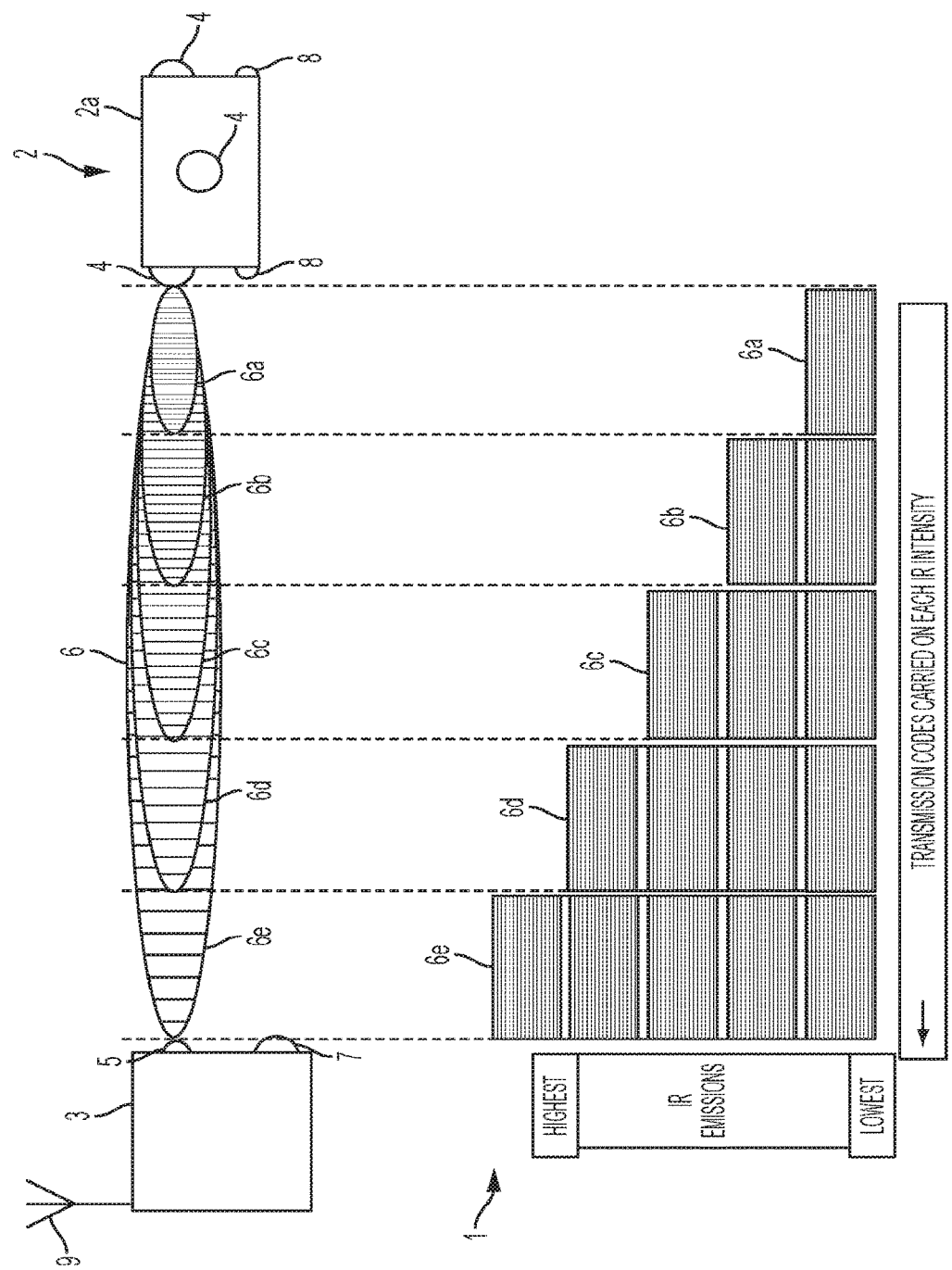
FIG. 1A illustrates an overview example of a badge transmitting a series of signals and primary receivers configured to receive these signals according to one embodiment of the present disclosure.
Figure 1B:
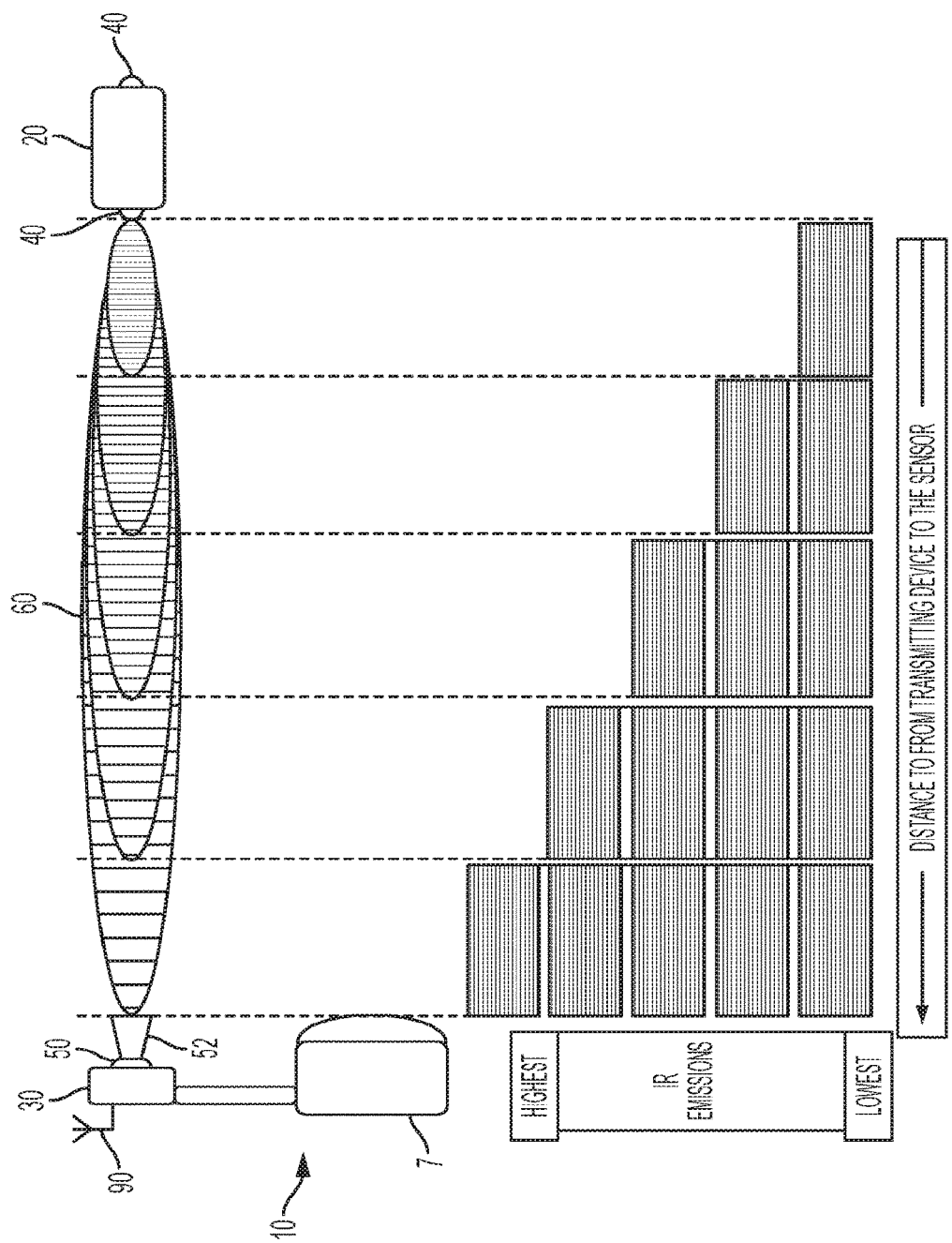
FIG. 1B illustrates an overview example of a badge transmitting a series of signals and primary receivers configured to receive these signals according to an alternative embodiment.

As generally shown in FIGS. 1A-B, a proximity, tracking, and location detection system 1, 10 according to embodiments of the present disclosure are schematically illustrated; and may include one or more tags, badges or other, similar devices 2, 20, which can be carried or worn by various persons or personnel in a selected facility, e.g., medical workers or patients in a health care facility, employees of a restaurant or manufacturing facility, and/or laboratory personnel, and series of primary receivers 3, 30 positioned at desired locations within preselected areas or environments throughout the selected facility, e.g., on the walls, doorframes, patient beds, washing stations, sinks, toilets, medical carts, or any other locations or areas in a medical facility where sanitizing or disinfecting actions are required and/or treatment or care to patients is provided. The locations of the primary receivers generally will be known, or in some applications, such as when mounted to a patient bed, can be identified with a known bed/patient identifier for coordinating the location/mapping of the badges detected thereby. In some embodiments, the primary receivers 3, 30 can be incorporated with/coupled to sanitation dispensers or other devices 11 at various sanitation stations located throughout a medical facility (FIG. 1B). However, embodiments of the present disclosure are not so limited, and it will be understood that the receivers 3, 30 can also be used in different environments or applications, such as in restaurants, manufacturing plants, laboratories, or any other facility or environment where monitoring and/or tracking of movements or activities of personnel is desired.

Figure 4:
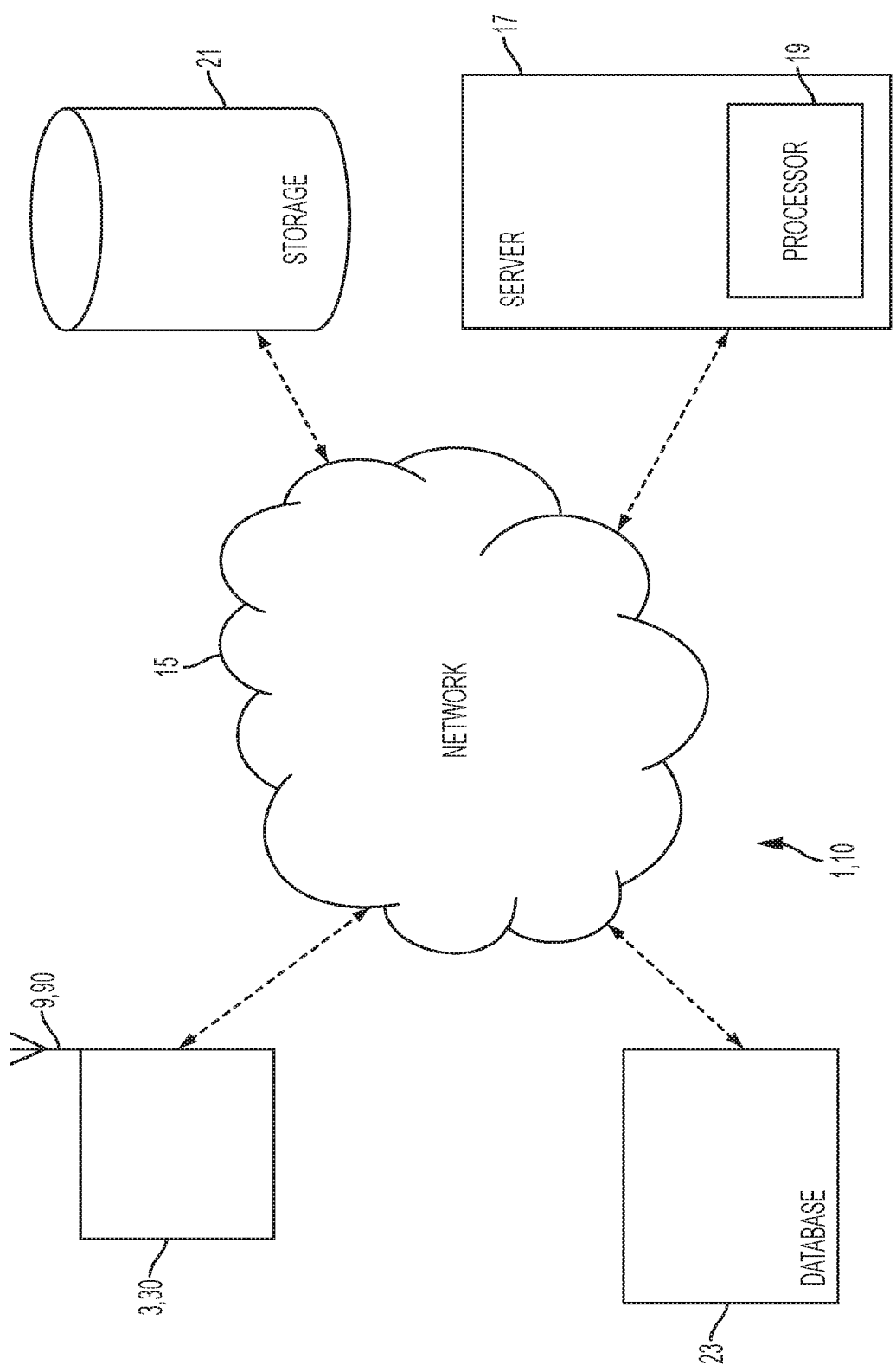
FIG. 4 provides a schematic illustration of communication between a primary receiver, a network, and a central processor according to embodiments of the present disclosure.

According to embodiments of the present disclosure, each badge 2, 20 can transmit a series of beams or signals 6, 60, which can be received or otherwise detected by one or more of the primary receivers 3, 30, and, based on such signals 6, 60, the location, proximity, or range of each badge 2, 20 and a specific transmitter signature or other identifier associated with the badge can be detected and captured by one or more of the primary receivers 3, 30. The badge/transmitter signature also can include signature information or signature identifiers sufficient to identify each badge and/or the person carrying or wearing the badge, such as by an employee number, patient code, or other suitable identifier. The primary receivers 3, 30 can further transmit this received information and information identifying the receiver such as a receiver identifier or other code, which can also identify a particular area or location where the receiver is mounted or located, to a network 15 in communication with a processor 19 to thereby allow for processing including real time tracking, identifying, locating, and/or mapping of the movements or activities of selected persons throughout the particular facility (FIG. 4). Although the present example discusses one or more badges transmitting a plurality of signals 6, 60 embodiments of the present disclosure are not limited thereto and may include tags, fobs, keycards, wristbands, or any other active or passive electronic device capable of being carried or worn.

Figure 2:
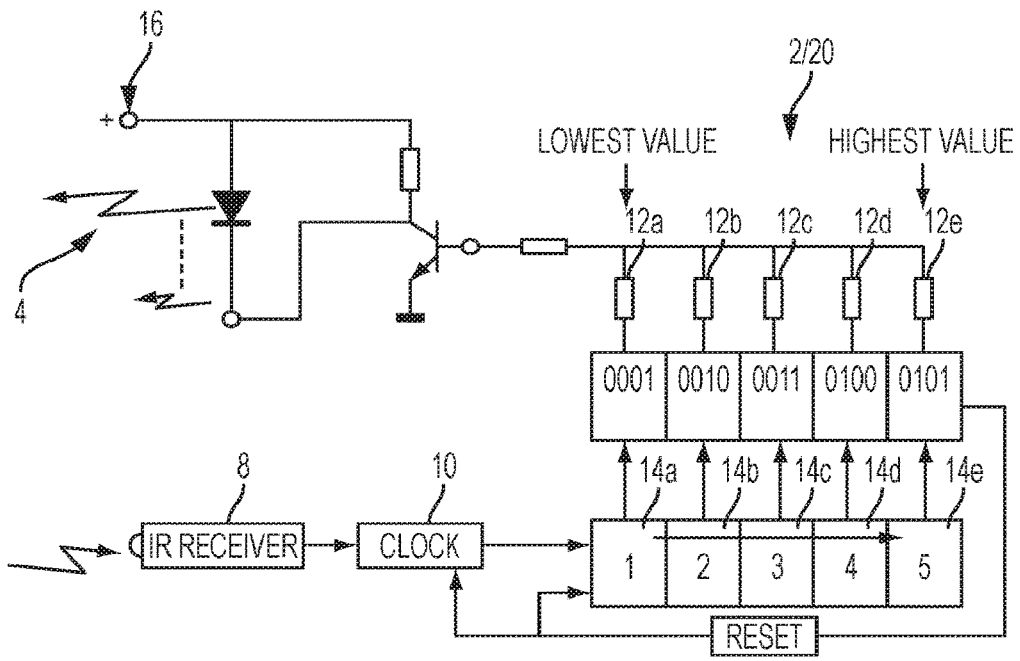
FIG. 2 provides a schematic illustration of the badge according to the embodiment shown in FIG. 1A.

FIG. 2 provides a schematic view of the badges 2 according to one aspect of the present disclosure. Each badge 2 may generally include a body 2a with front 2e and side 2b surfaces, and the badges may further include a primary transmission device 4, which, in one embodiment, can include one or more IR transmitters, such as an LED or an array of LEDs, for transmitting a series of IR signals 6a-6e. However, other transmission devices/signals also can be used. Each badge further can include a receiving device 8 configured to receive an activation signal for activating the badges 2, a timer or clock module 10, a series of resistors 12, one or more transmission modules 14, and a power source 16, such as one or more batteries. The primary transmission device 4 can include a series of LEDs disposed on various sides of the body 2a of the badge, such as two LEDs on opposite side surfaces 2b and one LED on a front surface 2c, which may face in a forward direction (e.g., away from a person's chest) when the badge 2 is worn or carried by selected personnel, though the primary transmission devices can be disposed or arranged in other configurations about the badge body 2a. The badges 2 can be activated and begin transmitting signals 6a-e when a receiving device 8 thereof, which may include an IR receiver, such as an IR receiving diode, photodiode, photocell, photo-emissive cell, photoconductive cell, photo-voltaic cell, photodetector, photosensor, light dependent resistor, light sensing circuit, or any other sensor for detecting electromagnetic signals, receives an initiation or activation signal from one or more of the receivers or other activation devices positioned at selected locations throughout the facility.

For example, in some embodiments, the primary receivers 3 may periodically or substantially continuously transmit one or more activation or initiation signals and, when the badge 2 is positioned/located or moves within a predetermined distance, proximity, range, or zone of the one or more of the primary receivers 3, e.g., when a person carrying or wearing a badge walks into a patient room or programmed or desired proximity, distance, range, or zone with respect to one or more of the primary receivers 3 disposed throughout selected areas of a particular facility, the badge receiving device 8 may receive, or otherwise detect, the activation or initiation signal and thereby activate or "wake up" the badge. The intensities of the activation/initiation signals can be selected so that transmission of such signals is contained within, or limited to, prescribed areas of the selected facility to prevent erroneous activation of the badges 2. For instance, primary receivers 3 or other activation devices can be positioned in a patient room in a medical facility and can transmit activation signals at intensities that will only activate badges 2 carried by a medical professional when he or she walks or passes through an entryway to selected areas of the medical facility or within a certain distance, e.g., approximately 1 ft. to approximately 2 ft., into the patient room to thereby prevent erroneous activation or initiation of the badge 2 when the medical professional simply walks by or only initially enters the patient room.

In one embodiment, once a receiver 8 of the badge 2 receives or otherwise detects an initiation/activation signal, the power source 16 can be activated and the badge can begin transmission of signals 6a-6e. The clock or timer module 10 can be configured to operate so that the signals 6a-e are transmitted in a selected or programmed sequence one after the other for a predetermined time period (or at other intervals). For example, each transmission sequence or burst can last for a time period of approximately 0.1 ms to approximately 10 ms with an intermission between each sequence of transmissions of approximately 0.1 ms to approximately 1 ms. It further will be understood that other varying and/or longer or shorter sequence intervals and/or intermissions also can be used. By way of example, the signals can be transmitted in cycles with the weakest signal first 6a and the strongest signal last 6e; however, embodiments of the present disclosure are not limited to such sequence and the signals 6a-6e can be transmitted in the opposite sequence, i.e., with the strongest signal 6e first and the weakest signal 6e last and/or in any other sequence. In addition, the badges 2 can reset the transmission of the signals after completion of a full sequence, such that the signals are transmitted in a periodic or substantially continuous cycle. Each badge 2 also can transmit signals 6a-6e in repeating cycles until the person carrying or wearing the badge 2 is no longer within the prerequisite proximity, distance, range or zone of one or more of the primary receivers 3 such that the receiver device 8 no longer detects or receives an initiation or activation signal, at which point the power source 16 can power down or the badge can enter a low power mode or "sleep state."

Additionally, the badges 2 can include a series of transmission modules 14a-e (FIG. 2) configured to produce a series of electrical signals or impulses for generating signals 6a-e, and each signal or electrical impulse can be modulated, controlled, or modified such that each signal 6a-e is transmitted with, or otherwise contains, signature information including a particular identifying code or unique signal identifier, such as a particular binary code decimal (BCD), alternative numeric signature, or any other identifier. For example, the power, amplitude, frequency, continuity, or other aspect or property of each signal can be modulated, modified, or controlled to generate the signature information, particular identifying code or unique signal identifier. The signals can include one or more components indicative of the signal strength/intensity of each transmitted signal, e.g., the identifying code signature identifier, and other components indicative of information corresponding to, or identifying each badge 2, which may include signature information or a signature identifier that may identify the person carrying each badge 2, with, for example, an employee id number, patient code, or other identifier. Each badge 2 further can include a series of intensity bias resistors 12a-e allowing for control of the transmission strength/intensity of signals 6a-e based on the resistance capacity of each resister, e.g., the higher the resistance of the corresponding resistor 12 the lower the signal intensity. It will also be understood that other methods and techniques for regulating the signal intensity also can be employed. Accordingly, each signal 6a-c can be transmitted at a predetermined intensity/signal strength based on the resistance capacity of resistors 12a-e, such that each signal can be received or detected at a predetermined distance, proximity, range, or zone and with a particular identifying code or unique signal identifier, such as BCDs: 0001, 0010, 0011, 0100, 0101.

For example, signal 6a can include identifying code or signal identifier 0001 and be transmitted at an strength or intensity such that it is received or detected within a distance, proximity, range, or zone of approximately 1 ft. radius around the primary transmitter; signal 6b can include identifying code or signal identifier 0010 and be transmitted at a strength or intensity such that it is received/detected within a distance, proximity, range, or zone of approximately 2 ft. radius; signal 6c can include a identifying code or signal identifier 0011 and be transmitted at a strength or intensity such that it is received/detected within a distance, proximity, range, or zone of approximately 3 ft. radius; signal 6d can include identifying code or signal identifier 0100 and be transmitted at a strength or intensity such that it is received/detected within a distance, proximity, range, or zone of approximately 4 ft. radius; and signal 6e can include a unique signal identifier 0101 and be transmitted at a strength or intensity such that it is received/detected within a distance, proximity, range, or zone of approximately 5 ft. radius. Though the present example embodiment is illustrated with five different signals with signal intensities/strengths varying at 1 ft. increments, any number of signals may be transmitted at any number of increments, including, but not limited to, one-four or a much greater number of signals, transmitted at increments of up to approximately 2-10 ft. or more or at much smaller intervals or increments such as approximately 10-5 in. or less.

In other embodiments, a substantially large number of signals can be transmitted from a badge to improve the precision or accuracy of the detection of the distance, proximity, range, or zone in which the badge can be received or detected. For example, up to approximately 100, up to approximately 1,000, up to approximately 10,000, up to approximately 100,000, or more signals varying with intensities can be transmitted from each badge. Transmitting such large numbers of signals can maintain a precise or accurate detection of the distance, range, proximity, or zone of the badges throughout continued use of the badges, such as through degradation of the components or at times of low battery power.

Figure 3:
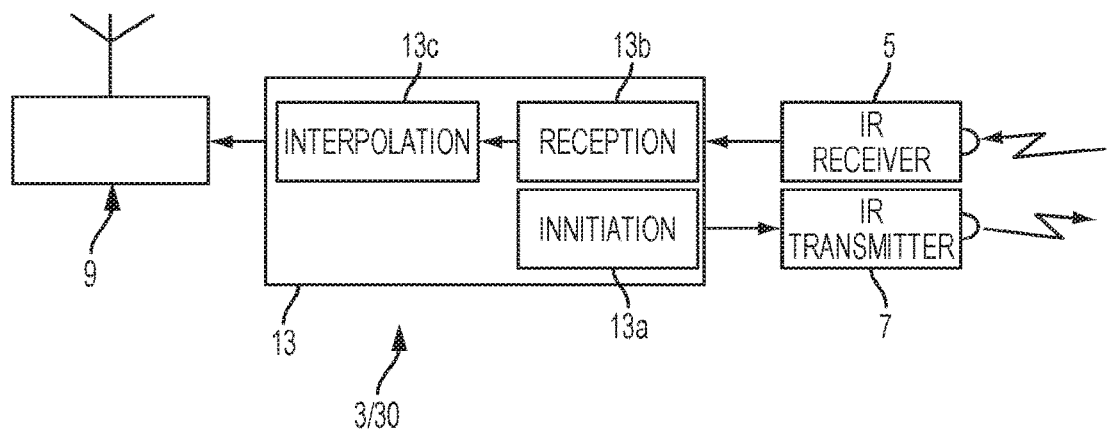
FIG. 3 provides a schematic illustration of the primary receiver according to the embodiment shown in FIG. 1A.

FIG. 3 provides a schematic illustration of the primary receivers 3 according to one aspect of the present disclosure. Each primary receiver 3 can generally include a receiving device 5, such as an IR receiver, which can include IR receiving diodes, photodiodes, photocells, photo-emissive cells, photoconductive cells, photo-voltaic cells, semiconductor devices, photodetectors, photosensors, light dependent resistors, light sensing circuits, or any other sensor for detecting electromagnetic signals, configured to receive, or otherwise detect, signals 6a-e; a first transmission device 7, which may include an IR transmitting LED; a processor 13 with a series of processing modules 13a-e; and a transmission device 9 for transmitting information based on the signal received by receiving device 5. The processor 13 can include an initiation module 13a that operates to control the IR transmission device 7 to transmit an initiation or activation signal to activate or "wake up" the primary transmitters 2. The processor 13 can also include a reception module 13b to initially processes/encode the signals 6a-e received or detected by the IR receiver 5 and send information corresponding to the signal or signals received to the interpolation module 13c. This interpolation module 13c can operate to interpolate information corresponding to the signal or signals received and can identify the particular received signal based on its unique signal identifier, e.g. BCD 0001. After one or more signals are identified, the interpolation module 13c can determine the approximate proximity, range, distance, or zone of the badge 2 to, or from, the primary receiver 3 and also identity information corresponding to the person carrying or wearing badge 2, such as a medical professional's employee number, based on the unique signal identifier of each badge. Such information can be collected into records or packets that can be sent periodically, together with the primary receiver identifier, to a central server/processor.

For example, if the interpolation module 13c identifies or determines that the receiving device 5 is only receiving signal 6e based on identifier 0001, the interpolation module 13b can determine that the badge 2 (and a person wearing the badge) is approximately 5 ft. away from the primary receiver 3, and alternatively, if the interpolation module 13c identifies or determines that the receiving device 5 is receiving all five of the signals 6a-e, based on identifiers 0001, 0010, 0011, 0100, 0101, the interpolation module can determine that the badge 2 (and a person wearing the badge) is approximately 1 ft. away from the primary receiver 3. The interpolation module 13c can then send, or communicate, this information, e.g. the proximity, distance, or range of the badge 2 and an identifier of the person wearing or carrying the badge, to a network 15 in communication with a server, central processor, computer (CPU), or central processing system 17 for further processing using transmission device 9, which may include an antenna, dongle, or other device for transmitting WiFi, Bluetooth, Radio Wave, or other electromagnetic signals. The receivers 3 can also transmit information identifying the receiver, such as a receiver identifier or other code corresponding to each receiver which may be indicative of a particular room, location, or area where the receiver is located in the facility.

According to an alternative embodiment, the primary receiver 30 may include one or more prisms 52 designed and configured to receive signals 60 transmitted from a badge 20, which may be directed at a series of predetermined angles as shown in FIG. 1B. The one or more prisms 52 can be located and/or oriented to receive an IR transmission from the transmitter 40 (badge and/or other static or moving unit containing ID signature, location and distance) and can reflect the beams/input onto an IR sensor or sensor array 50. Each receiver further can send collected records or data to the network 15, which is in communication with server 17, via an antenna 9 using any available communication system (e.g., WiFi, Bluetooth®, radio, IR system). Each badge 20 can again have a unique ID signature, such as a BCD or other suitable identifier, and the receiver 30 can decode each specific signature and send this information through the network to a central monitoring system or server 17 where the data can be stored in a storage 21.

As illustrated in FIG. 4, after one or more signals are detected by the one or more of the receivers 3, 30, information corresponding to the signature information contained within the received signal identifying the badge or others unique identifier, and information identifying the receiver or receivers 30 can be transmitted wirelessly, in real time, to a network 15, such as a cloud based network, virtual personal network (VPN) or local area network (LAN), via a transmitter 9, 90, such as a Radio Wave, Bluetooth®, WiFi, IR, or other electromagnetic transmitter, in communication with the receiver 3, 30. This information, as well as any additional recorded information associated therewith, can then be transmitted to a server, computer, or central processing system 17, which is in wireless or direct communication with network 15 and includes a processor 19 operable to perform processing on the information corresponding to the unique identifiers of the signal or signals received, such as track or measure specific, predetermined, desirable or undesirable activities or movements or to detect the activation of a device such as a soap or antibacterial dispenser 11. Accordingly, embodiments of the present disclosure can be used to track restaurant, food manufacturing, or medical employees' or patient's movements, location and activities throughout a predetermined space, for example, a patient room or an isolation ward. In one example, one or more receivers 3, 30 can be incorporated into, or otherwise in communication with, a sanitation device, sanitizing fluid dispenser or other device 11 (FIG. 1B) and/or mounted, or otherwise disposed on, a door, cabinet, monitoring or other patient treatment equipment, and/or other suitable items, and the one or more receivers 3, 30 can signal the processor 19 when activated. For example, the system can detect when a restaurant employee enters a bathroom, and detect if and when that specific person activates a soap or disinfection dispenser, or not, within a predetermined time period.

Additionally, the system may include a database 23 connected to, or in communication with, the network 15 and the processor 19, and the data stored in this database 23 may include information related to the patients checked into and/or medical professional workers working at a medical facility. For example, this data may include patient medical records, such as any communicable or infectious diseases/ infections the patient has contracted, and the data may also include information relating to the time and date the patient checked into the medical facility, the duration of the patient's stay at the medical facility, the particular area, location, or room to which the patient is assigned and/or other medical facilities the patient has visited. This data may be organized in the database 23 based on a patient identification/tracking number which may include a patient's date of birth, Social Security number, or other identifier. As a result, the tracking records provided by the system 1, 10 may be used to cross-reference information including the location (e.g., the proximity, range, distance, or zone between a selected badge and one or more receivers) and identifier of the badges and information, including the location and an identifier of one or more receivers with the information stored in the database 23 to track or map a particular person's movement through a medical facility and, based on such tracking or mapping, can potentially determine whether such person came in proximity to, or was otherwise exposed to, a particular infection or disease, such as staph, MERSA, Ebola, or other communicable infection or disease.

Figure 5:
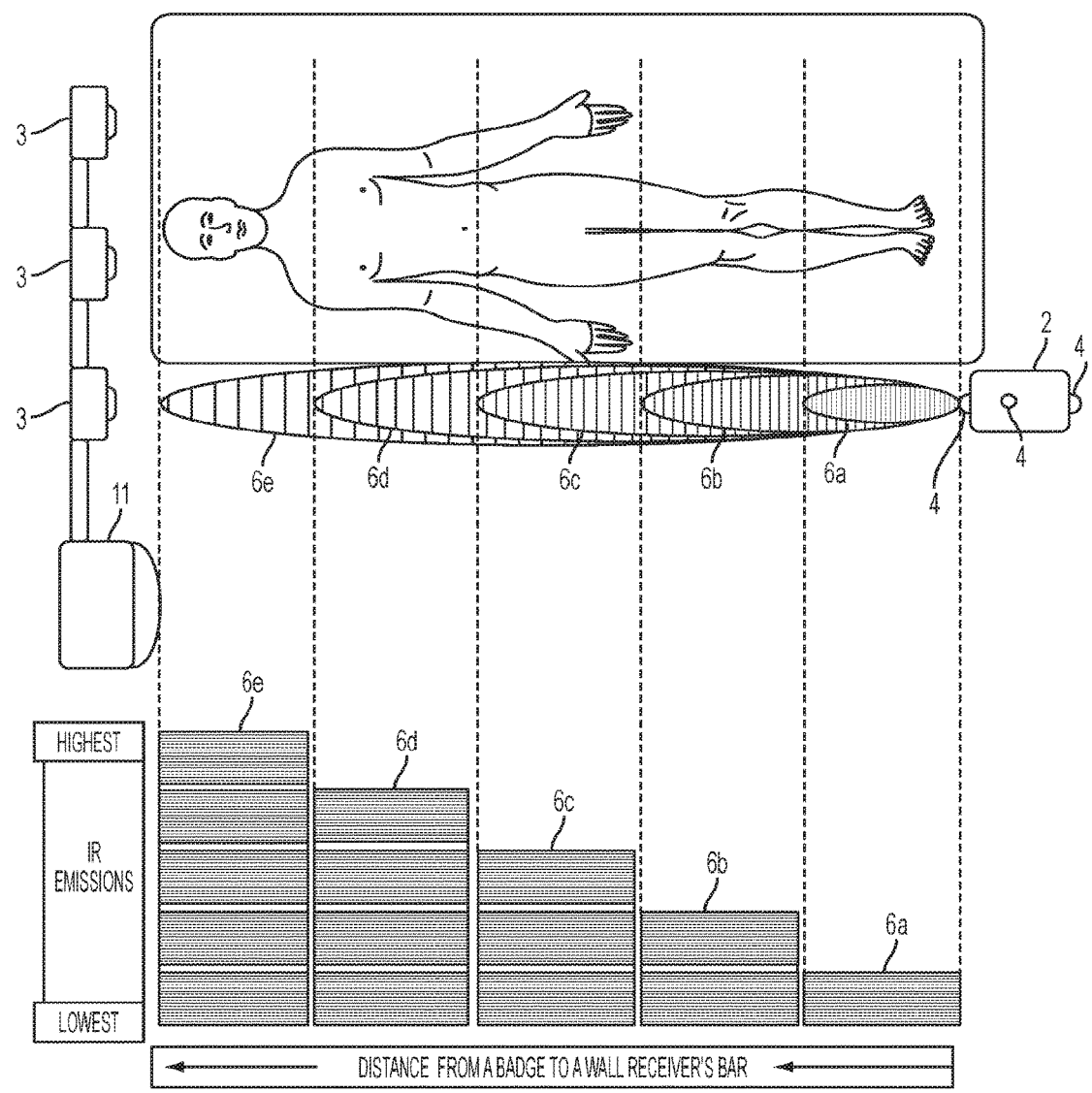
FIG. 5 provides an overview example of a badge transmitting signals to a series of primary receivers disposed near the head of a patient bed according to one example embodiment.

FIG. 5 shows an example embodiment of the present disclosure in which one or more primary receivers 3 are disposed near the head of a patient's bed and/or at other locations such as on the wall behind the patient's bed, on the bedpost, or in a medical diagnostic device positioned near the head of the patient's bed. In this example, each badge 2, which can be worn or carried by a medical worker, can activate or "wake up" when the worker steps within a predetermined distance, proximity, range, or zone of the patient's bed and the badge 2 receives an activation or initiation signal from one or more of the primary receivers 3, as described. Alternatively, one or more primary receivers 3 or other activation devices can be disposed near an entryway, e.g., doorway, of the patent's room, such as on, or in, the doorframe, so that each badge 2 activates immediately when the medical worker carrying or wearing the badge enters the patient's room.

Once the badge 2 is activated, the one or more primary transmitting devices 4 of the badge can begin to transmit the series of signals 6*a-e*, and when, for example, an initial primary receiving device 3 receives one or more of the signals 6*a*-6*e*, a sanitizing device 11, connected to, or in communication with, such a primary receivers 3 can indicate to the medical worker that a sanitation action is required. For example, the sanitizing device 11 may include one or more LEDs, or an alarm, that may illuminate, or sound, to indicate that a particular sanitation action is required. Additionally, the primary receiver 3 may encode or capture the unique identifier identifying the particular worker contained within the signals 6*a*-6*e* and may transmit, or otherwise communicate, the unique identifier and other information to the central server 17 (FIG. 4) through the network 15. By way of example, one or more of the primary receivers 3 may transmit the identifier of the worker and a receiver identify or other identifier identifying the particular primary receiver or receivers 3/30, which received one or more of the transmitted signals from the badge(s), and the primary receiver 3 may also transmit information corresponding to whether the sanitizing device 11 was used or activated. This may allow for real time tracking of the specific location of the medical professional in relation to a particular patient or patients and compliance by the medical worker with the alerted sanitation action. This information, e.g., the worker's identifier, the primary receiver's identifier, and information on whether the sanitation device was activated, can further be stored in storage 21 for mapping of the particular patient visited and whether the medical worker complied with the alerted sanitation action.

In addition, embodiments of the present disclosure may provide for a determination of improved precision in tracing or mapping movements and/or an area or location(s) on or along the patient's body where the healthcare worker provided treatment or may have contacted the patient, since the worker's position with respect to the patient can be identified based on the particular signal or signals received, as described. By way of example, if a wall or bed mounted primary receiver 3 identified with the patient receives only a first signal 6*e*, it can be determined that the medical worker wearing or carrying the badge came within a desired or predetermined proximity to the patient's feet or lower legs; if the primary receiver 3 receives signals 6*c*, 6*b*, and 6*a*, it can be determined that the medical worker carrying or wearing the badge is within a desired or predetermined proximity to the patient's torso, and if the primary receiver 3 receives all signals 6*a-e*, it can be determined that the worker carrying or wearing the badge is within a desired or predetermined proximity to the patient's head. Records of the received signals or codes indicative of the detected location(s) of the medical worker in relation to the patient's body together with the badge identifier identifying the medical worker, can be collected and/or stored as records that can be transmitted, together with a unique code identifying the primary receivers 3 that received and collected the record of these badge transmitted signals 6*a-e* to the processor 19. Alternatively, a simple signal 6*a* can be transmitted by each badge, and based upon a detected intensity or strength of signal thereof, as a result of its proximity to or distance from the primary receiver, can be monitored to determine and/or map locations of the badge wearer with respect to the patient's body. Additionally, each primary receiver 3 may also measure the specific number or amount of time each of the signals 6*a-e* is received and encode these measurements and transmit them to the processor 19.

Based on the unique code identifying the primary receiver or receivers 3 providing each record received by the processor, the processor 19 can identify the patient being treated and can then access the patient's medical history from the database 23 to determine whether a medical worker designated to provide a prescribed treatment to the patient has visited the patient or has yet to complete such a visit by cross-referencing whether the signal(s) received correspond to the designated worker, with the patient's medical information, and if so, monitor the duration of their visit and location(s) with respect to the patient's body can be used to substantiate/check their visit. For example, if the patient has an injury or a malady on his or her foot or lower leg, e.g., gangrene, this will be indicated in the patient's medical records stored in database 23, and the processor can determine whether the designated medical worker both entered the patient's room and actually approached the patient and/or was in proximity to the injured area to an extent sufficient to provide requisite treatment thereto. As a further example, if the patient has an injury to their head, e.g., a blunt force trauma, and the identified badge/professional treating such an injury is detected by the primary receiver 3 (FIG. 5) receiving a strength/intensity signal indicating they did not approach the patient's head, or all received signals are received for less than a required or expected duration for the medical worker to provide the requisite treatment for such a trauma, the processor 19 can indicate/attach a note to such a record and/or call for a check/confirmation that the designated worker or another worker has provided the proper treatment to the patient.

Additionally, based on a detected location or locations of a healthcare worker, as identified by the signal or signals received and/or recorded from one or more identified primary receivers within the facility that have detected the worker's badge, the processor 19 can determine whether the healthcare worker was exposed to any communicable diseases or infections possessed by the patient, such as MRSA, staph, or Ebola, which may have been communicated to the healthcare worker. For example, if the patient possesses a communicable infection/disease on his or her foot and the medical worker comes with in a certain proximity to the patient's foot (e.g., approximately 0.5 in to approximately 2 ft. or any other distance, range, or proximity sufficient to contract the infection/disease) the processor 19 can determine that the medical worker potentially was exposed to the communicable infection/disease by cross-referencing the signal received from the badge of the medical worker, e.g., only signal 6e received, with the patient's health information or medical records indicating the communicable infection/disease on their foot. This can therefore allow for mapping of the movements and activities of the healthcare worker throughout the medical facility, including mapping or logging the particular communicable infections/diseases in which a particular healthcare worker encountered or was exposed to. Accordingly, real time tracking and mapping of all of the communicable diseases each person, e.g., healthcare workers or patients, in the facility has been exposed to can be achieved. Further, the processor 19 can generate forensic maps showing the particular positions of each of the persons in the medical facility, e.g., patients and healthcare workers, and the particular diseases or infections they were potentially exposed to and further store such maps in storage 21.

According to further aspects of the present disclosure, by cross-referencing the position of the healthcare worker based on the signal or signals received by the primary receiver(s) 3/30 and the health information or medical records of the patient, the processor 19 can determine a particular sanitation action the healthcare worker is required to take and communicate such action to the health care worker. In this example, each badge worn by healthcare personnel can include one or more altering or indication devices, which may include a series of LEDs, or an audible alarm, which can be a speaker(s) or other audio device, and the altering or indication devices can alert healthcare personnel to take particular sanitation actions, such as by executing a particular illumination sequence of the LEDs or sounding a predetermined number of tones with the alarm. Accordingly, based on a patient's particular health information stored in the database 23, including any communicable diseases or infections the patient may have, the processor 19 can determine what particular sanitation actions are required and transmit a signal containing information to the primary receiver or receivers 3 receiving signals from one or more badges 2. This information can then be relayed from the primary receivers 3 to the badges 2 to activate a particular sequence, or specific color (e.g., red), of the LEDs or sound a specific tone or number of tones of the alarm to communicate whether, and which, sanitation action may be required.

For example, if a patient does not have a serious infection or disease, the processor can determine by cross-referencing the identified receivers located in the treatment area housing the patient and reporting contact with a monitored medical worker (i.e., by detector of their badge) with the patient's medical information stored on the database, and thereafter can transmit information to the one or more receivers and/or to the badges so that only a single LED may illuminate or only a signal tone may sound from the audible alarm, such as to indicate that minimal sanitation is required, e.g., washing hands or using hand sanitizer, and on the other hand, if the patient has a serious infection or disease, all of the LEDs on the badge may illuminate or produce a specific color or the alarm make sound numerous tones or a specific tone to indicate that a higher level of sanitation is required, e.g., changing of clothes, quarantine, or other disinfection procedure. The primary receivers 3 and the sanitation devices 11, which may be coupled thereto, may also include a series of alerting/indication devices, such as LEDs or alarms that can light up in a particular sequence or with a particular color or make a series of sounds or tones to indicate various sanitations action required.

Additionally, if the medical worker does not take a particular sanitation action (e.g., does not activate or come within a certain proximity of a sanitation device) after coming within a particular area or zone, such as a zone or area with patients having a particular serious disease, the indicators on the badges or receivers can execute a particular LED illumination sequence or color or sound a distinct tone or number of tones to indicate a required sanitation action, e.g., change clothes or wash hands.

In a further example, the badges 2 may provide access to selected areas of a medical facility, e.g., patient rooms, such as by activating door locks coupled with RFID receivers. Accordingly, by cross-referencing the patient information or medical history of the patients in different areas of the medical facility with the identifier of, and other information relating to, the medical worker carrying or wearing the badge 2, the processor can determine which workers should or should not be granted access to various areas of the facility to thereby ensure only properly trained or qualified medical personnel are allowed to enter various selected areas. In one example, the processor can cross-reference medical information of patients in selected areas of the medical facility, including information on any infectious/communicable diseases the patient(s) may have contracted, in view of received information identifying the badge, which can also identify the medical working carrying such badge and other information on the medical worker, which may also be stored in the database; and, can determine whether such identified medical professionals are permitted entry to the various selected areas of the medical facility based on this cross-referenced information. If a medical worker is determined not to be qualified to treat a particular disease or infection, such medical worker's badge may not permit or grant them access into areas of the medical facility housing patients with such particular disease or infection.

In another example, the system can grant or permit access only to medical workers who have already taken the proper preparatory procedures to encounter patients with a specific infection or disease. For example, if a medical worker is required to put on a hazmat suit or other protective clothing or to take certain precautions/procedures prior to entering a patient area, detection of the medical worker's badge may generate a signal to grant access to the particular area only after detecting the worker clears the required precautions, or alternatively, if a secondary badge linked to a receiver 3 of the hazmat suit or other protective clothing is detected. As another alternative, the medical worker may have to swipe, or hold their badge within a close proximity (approximately 0.5 in. to approximately 3 in.) to a receiver contained in the hazmat suit or other protective clothing. For example, the hazmat suit or other protective clothing may have one or more transmitting devices transmitting a code or identifier specific to each hazmat suit or other protective clothing, and the badge will not be permitted into the selected areas requiring such additional protection unless the signal from the badge is received along with a signal from the transmitter of the suit or protective clothing.

In a further aspect of the present disclosure, the system 1, 10 can track and identify equipment or personnel entering or passing through a series of predetermined zones or sub zones, the time the person identified with a certain badge 2, 20/IR transmitter ID or signature remains in such zones and sub zones, and use or non-use of specific equipment in such zones or sub-zones. For instance, in medical facilities (drug rehab, nursing homes, hospitals, medical offices, etc.) personnel can be tracked in proximity to drug cabinets, hazardous areas, patient areas; and predetermined desirable or undesirable actions can be detected, such as cabinets/doors opening or closing, dispensers used or not used, equipment handled or not handled, areas approached or not approached. In each event detected and/or recorded, the data received by the processor 19 will be in real time and recorded for that specific signature. Multiple predetermined events according to the application and/or environment, e.g., hospital, food service, clean room, etc., in which the system is used, such as proximity to a dispenser and/or a receiver, use of a dispenser or a tool, and/or tracking through predetermined zones, can be read for each specific transmitter signature.

According to further embodiments, which can include features that can be used with and/or incorporated into the above exemplary embodiments or that can replace various features of the above exemplary embodiments, embodiments of the present disclosure can be adapted for use as a tracking and proximity warning system for us in hospital patient rooms to help facilitate compliance with sanitizing and/or disinfection procedures and practices.

Figure 6:
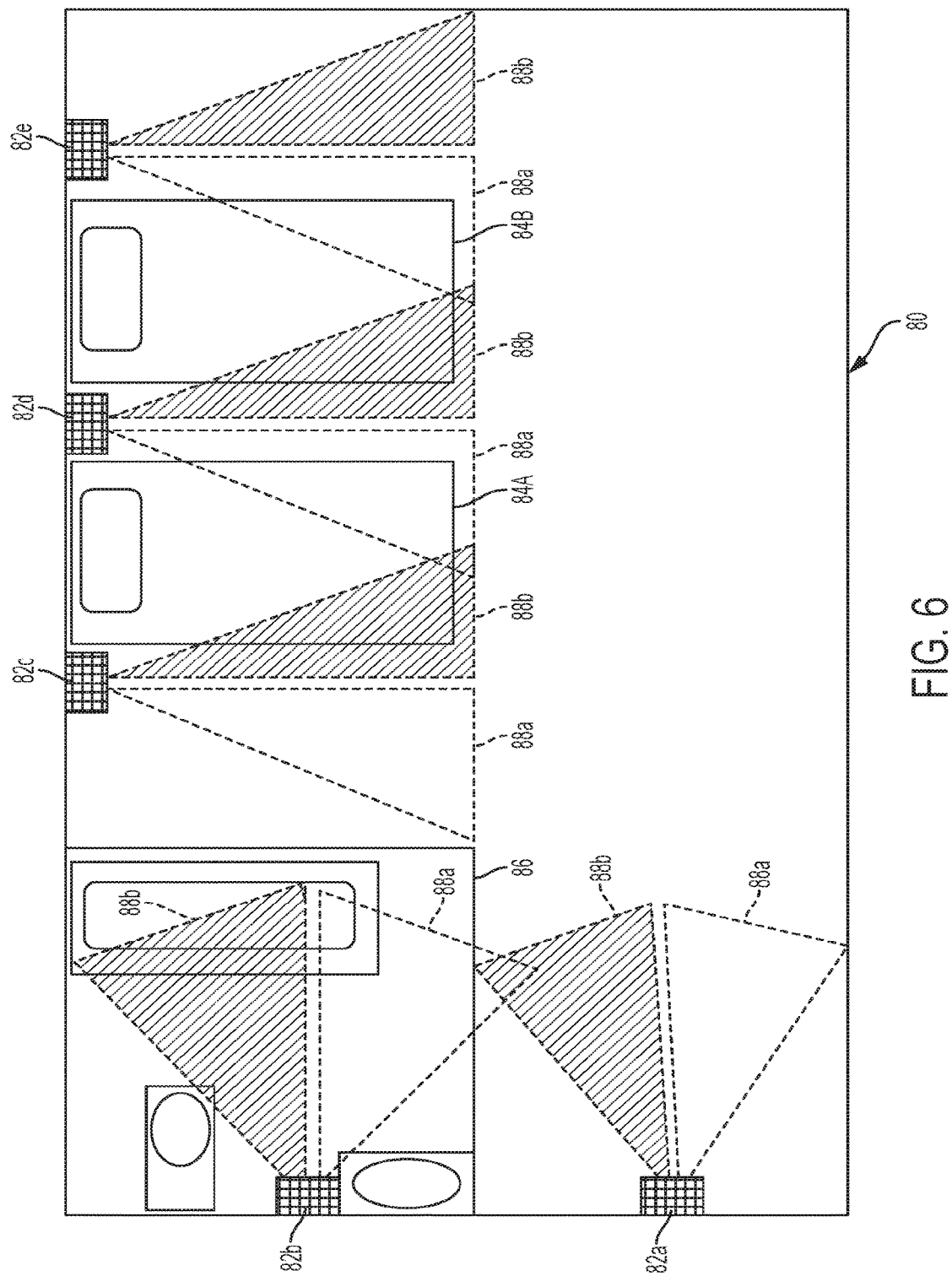
FIG. 6 illustrates a series of primary receivers and subzones generated thereby in a patient room according to an additional aspect of the present disclosure.

In an additional embodiment of use of the compliance system according to the principles of the present disclosure, FIG. 6 illustrates operation of the IR subzone technology in one example embodiment incorporating a sanitizing or disinfecting fluid dispenser system set in a hospital patient room 80. There are five dispensers 82a-e, in this example showing the layout of a semi-private patient room 80 including two beds 84A-B. Private or semi-private patient rooms are typical in most U.S. hospitals, but other countries frequently have multiple beds in a room. Depending on the size of the patient room, a minimum of three sanitizers/soap dispensers 82c-e can be positioned to track the presence of a healthcare provider proximate to beds 84A/B and side of the beds approached. In the present example, there are four sanitizer stations 82a and 82c-e and one soap dispenser station 82b, which can each incorporate, or otherwise be in communication with, primary receivers 3, 30, positioned along two of the walls of the room 80. Specifically, a sanitizer dispenser 82a can be at the entrance/exit of the room and a soap dispenser 82b can be located adjacent or internally to a bathroom 86 are shown. There can also be sanitizers 82c-e along another wall and behind the patient beds 84a/b. The primary receivers 3, 30 coupled to, or incorporated with, each dispenser/sanitizer can have an infrared emitter, e.g., transmission device 7, and a detector, e.g., receiving devices 5, 50, that can illuminate two subzones 88A/B that emanate from each dispenser 82a-c, and that receive infrared signals from badges 2, 20 carried by various hospital personnel. However, embodiments of the present disclosure are not limited to two zones or subzones and only a single zone or more than two zones or subzones may be used for each dispenser.

As further shown in FIG. 6, in a two bed-three dispenser scenario, the placement of dispenser 82c creates two subzones 88A/B, one of which provides coverage of the space to the left side of the first bed. The two subzones 88A/B created by dispenser 82d cover the space to the right side of the first bed and to the left side of the second bed. For the two subzones created by dispenser 82e, one covers the space to the right side of the second bed. With this example, zone 88A for dispenser 82c and zone 88B for dispenser 82e are too far from the left and right beds, respectively, to trigger an audio alarm or visual signal to a hospital worker, but any badge 2, 20 detected in these zones will also be identified, tracked, and monitored. In order to fully utilize the IR subzone technology in a hospital environment, each healthcare worker or patient can carry or wear badges 2, 20, which can transmit signals with individualized signatures or other identifiers. The badges 2, 20 can also respond illumination signals emitted by the primary receivers 3, 30 coupled to the dispensers 82. FIGS. 7A-B illustrate top and side views, respectively, for subzones of badges 2, 20 worn by such personnel or patients. FIG. 7A shows four subzones 90a-d that can be generated by the badges 2, 20 receiving and responding to illumination emitted from a dispenser. The four subzones emanating from the primary badges 2, 20 cover approximately 180 degrees horizontally from the healthcare worker. FIG. 7B indicates that the badges 2, 20 may emit a signal that provides a significant amount of vertical coverage from the healthcare worker. The coverage provided both horizontally and vertically facilitates placement of the dispenser at various vertical positions along the room wall.

In a further exemplary embodiment, infrared technology can be combined with subzone technology to determine worker sanitation compliance utilizing one or more smart dispensers, which may house or incorporate primary receivers 3, 30. The primary receivers 3, 30 of the smart sanitizer or soap dispensers can, for example, generate a single IR source to create one or more IR dispenser subzones each having a unique address. Accordingly, any smart dispenser, with primary receivers 3, 30, can track or locate a worker, who can be carrying a badge 2, 20, throughout a particular subzone location, and thus, each smart dispenser can track and monitor such worker's movement and activities throughout different subzones and/or determine the total time spent by the worker in each subzone. Additionally, each badge 2, 20 carried by workers can also utilize this subzone technology. For example, each badge 2, 20 can generate a single IR source to create multiple IR badge subzones and each multiple IR badge subzone can have the same unique ID address. Further, the badges 2, 20 can activate or wake up after entering any of the one or more IR dispenser subzones and transmit the unique badge ID to the dispenser and then go back to sleep. Accordingly, combining one or more IR dispenser subzones throughout a selected a work area with IR badge subzones can allow for identification and monitoring of the position and movements of a worker in real time to ensure compliance with sanitation requirements.

In an additional alternative embodiment, the present disclosure provides an infrared identification tracking method and system for hospitals and/or food processing hygiene compliance. In this embodiment, each medical worker or healthcare professional can wear a badge 101, or badges 2, 20, on their chest. Each badge 101 can comprise, for example, at least three infrared LED's 102-104, in a configuration as shown of one LED in the front 102 and one LED on each side 103/104. This configuration provides a coded person's identification and position within a predetermined zone. The predetermined zone can be designated by several factors, such as, distance, front, right, left side seen from the orientation of the badge 101. The badge 101 may also include at least one infrared receiver 105 that functions to "wake up" the badge 101 when the badge receives a signal from a dispenser or other tracking unit, such as those that are installed within a facility. Generally, the badge 101 can be in a ready state and can be woken up in order to provide for battery saving.

Figure 8:
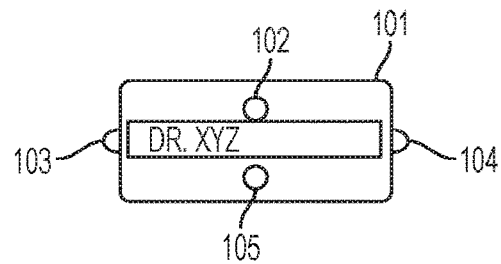
FIG. 8 illustrates a badge according to an alternative embodiment of the present disclosure.

As shown in FIG. 8, each badge can include a badge body indicated at 101, a center infrared LED indicated at 102, a right side LED indicated at 103, and a left side LED indicated at 104, and a wake-up infrared sensor indicated at 105. The badge shown in FIG. 8 also includes an identification (as shown, this badge belongs to "Dr. XYZ"). The compliance system then coordinates multiple hygiene dispensers installed in, for example, a patient's room. Additionally, each of the dispensers generally comprises at least one infrared transmission LED, at least one front infrared receiver, at least one side infrared receiver, at least one infrared sub-zone on at least one side of the unit, and a Radio Frequency (RF) transmitter. The RF transmitter generally sends any event to the cloud through an antenna, which can be received by a central facility computer to be recorded and processed. Still further, the system can be provided with an exit room location tracking infrared relay or detector, which can be comprised of an IR receiver and an IR and/or RF transmitter. The system can send a signal when the person wearing the badge, generally a health care worker, leaves the patient's room, or any other location in the facility identifying the badge wearer's location.

Figure 9:
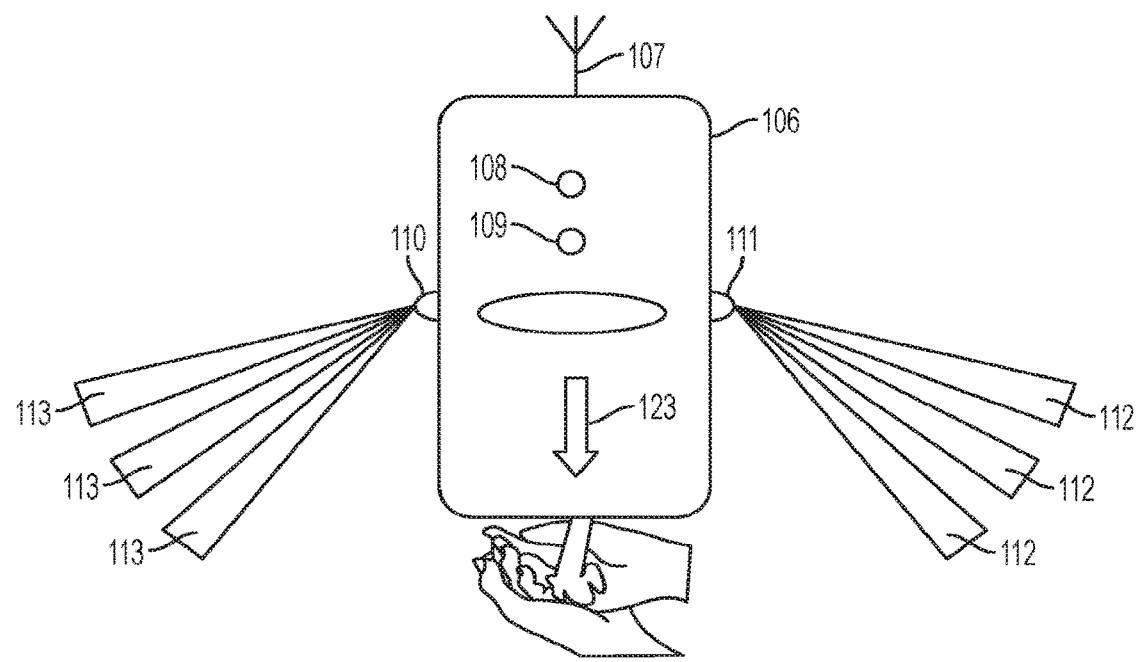
FIG. 9 illustrates a dispenser according to the embodiment shown in FIG. 8.

FIG. 9 shows a dispenser 106 generally positioned within the facility. The dispenser shown in FIG. 9 can optionally include internal side subzone receivers 110/111. The dispenser includes a dispenser body, generally indicated at 106, an RF antennae, generally indicated at 107, an infrared front receiver, generally indicated at 108, an infrared transmitter, generally indicated at 109, infrared left side receivers array (internal receivers), generally indicated at 110, infrared right side receivers array (internal receivers), generally indicated at 111, infrared right side receivers subzones, generally indicated at 112, infrared left side receivers subzones, generally indicated at 113, and a timer, as shown, generally indicated at 123, which timer can include a delay (such as a 10 second timer) and can include a visual indicator, such as a blinking arrow as shown in FIG. 9.

Figure 10A:
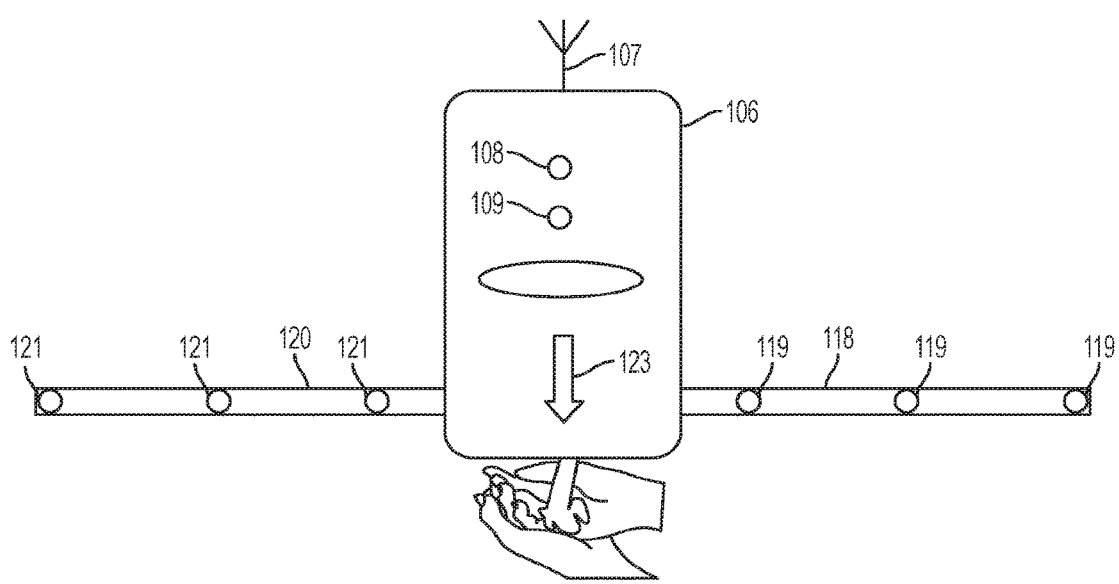
FIG. 10A illustrates the dispenser of FIG. 9 with a side bar and zone receivers.
Figure 10B:
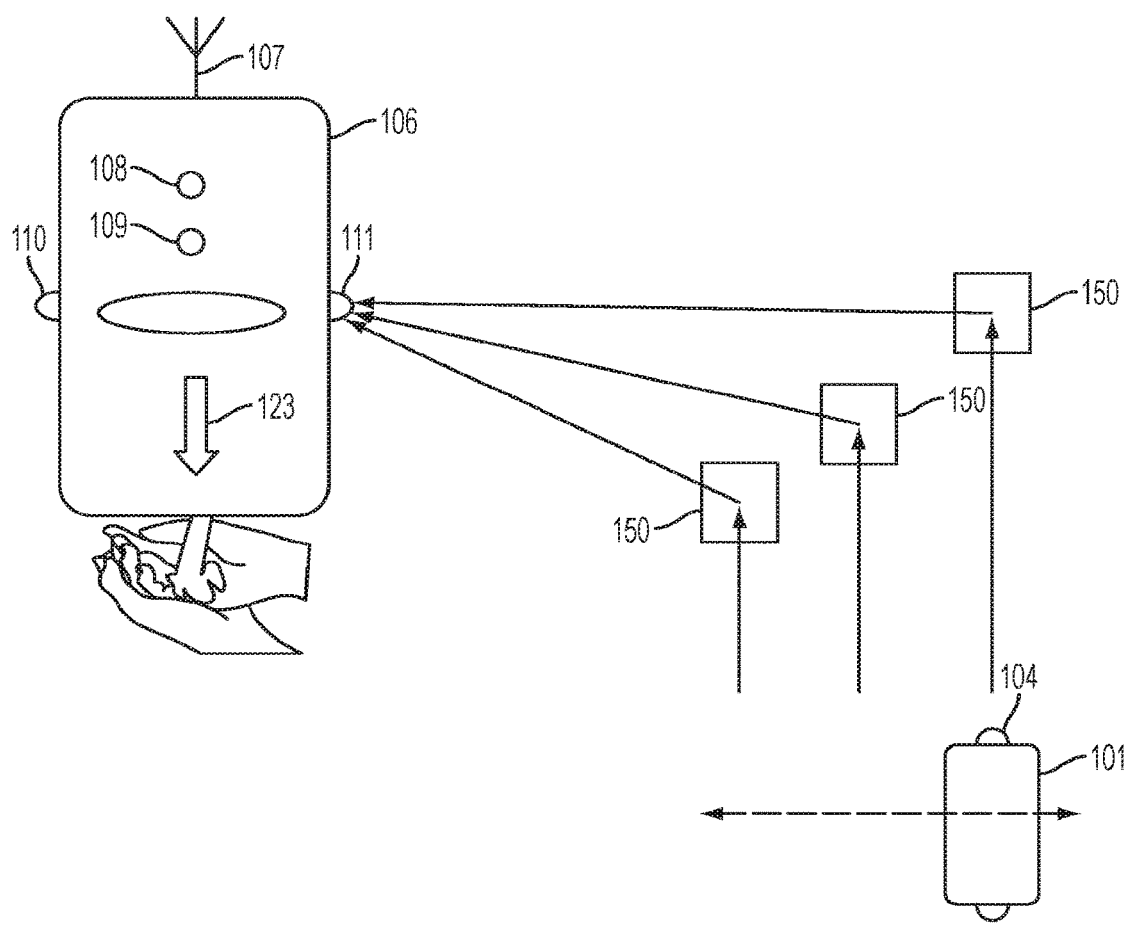
FIG. 10B illustrates the dispenser of FIG. 9 with mirrors for reflecting a transmission to the dispenser.

FIG. 10A shows a dispenser with side bar sub and zone receivers. As shown in FIG. 10A, the dispenser includes left sub zone bar 120, right sub zone bar 118, right infrared constant sensitivity sensors 119, and left infrared constant sensitivity sensors 121. FIG. 10B illustrates another option for detection of sub zones and distance detection data can be achieved by replacing one of more of the IR receivers 119 of FIG. 10A with mirrors 50 that can be adjusted to reflect the received transmission from a badge 101 respective LED 4 to the receivers 111, which are located on each side of the dispenser 106 in one embodiment.

Figure 11:
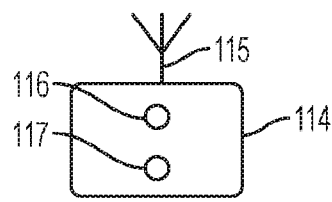
FIG. 11 illustrates an exit room and tracking unit that can be used in the embodiment of FIG. 8.

FIG. 11 shows an exit room and tracking unit. As shown in FIG. 11, the exit room unit and tracking unit includes a body, generally indicated at 114, an RF antennae (optional), generally indicated at 115, an infrared receiver, generally indicated at 116, and an infrared transmitter, generally indicated at 117. When a caregiver is leaving the patient room, the unit receives a signal from badge 101, and transmits an exit signal with badge ID to the dispenser 106 via front receiver 108, and optionally, to the network 15 via antennae 107. This signal transmission will allow the badges to reset back to the beginning mode.

Figure 12:
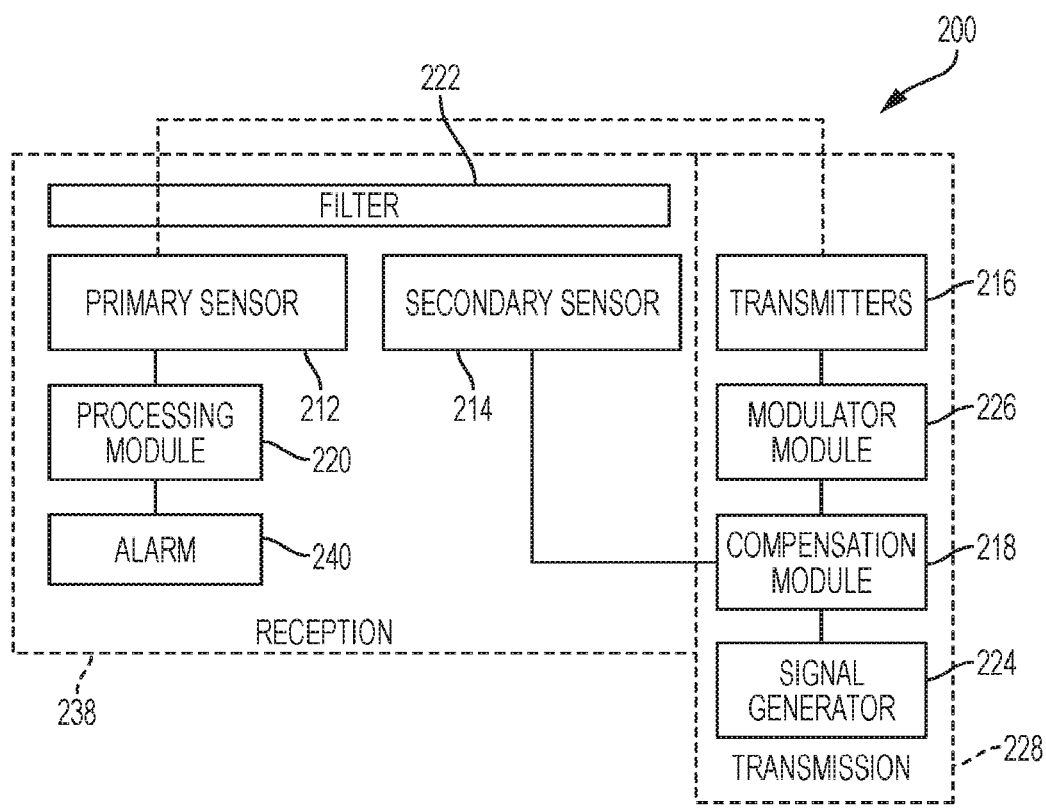
FIG. 12 illustrates a block diagram of a proximity warning system, constructed and operative according to example teachings of the present disclosure.

FIG. 12 shows a schematic of one embodiment of the proximity warning system, generally designated 200, constructed and operative according to embodiments of the present disclosure, for warning of the proximity of an obstacle within at least one zone of interest. Generally, system 200 includes at least one primary sensor 212 deployed to receive radiation from at least part of the zone of interest. Primary sensor 212 is configured to produce a primary output indicative of a quantity of electromagnetic radiation incident on primary sensor 212. System 200 also includes means for generating a compensation output indicative of a quantity of background electromagnetic radiation incident on primary sensor 212. At least one transmitter 216 can be configured to transmit an electromagnetic signal towards at least part of the zone of interest. A processing module 220 is responsive to the primary output of primary sensor 212 to generate a warning signal.

Turning now to the features of the system 200 in more detail, according one exemplary embodiment, the means for generating a compensation output includes at least one secondary sensor 214 for measuring the background radiation. In this case, primary sensor 212 can be configured to be sensitive to a first range of wavelengths, while secondary sensor 214 can be configured to be sensitive to a second range of wavelengths. By configuring transmitter 216 to transmit an electromagnetic signal at a wavelength falling within the first range but outside the second range, the secondary sensor is rendered insensitive to the transmitted signal and measures only the background radiation.

In order to ensure that the measured background is reliably indicative of the background radiation level in the wavelength range measured by primary sensor 212, the first and second ranges are preferably relatively close parts of the spectrum. In one implementation, the transmitted electromagnetic signal lies within the near infrared portion of the electromagnetic spectrum. Particularly when used in combination with an optical filter (described below), which selects the red end of the visible spectrum, the measured intensity of the visible sunlight radiation can provide a near-infrared signal of approximately near-infrared sunlight intensity.

Both primary sensors 212 may be of any commercially available type sensitive to the wavelength bands of interest. Typically, such sensors are made up of a photodiode with appropriate prefiltration and an associated electrical circuit to generate a current output as a function of the incident radiation intensity within the given range. However, any other type of sensor capable of producing a signal indicative of the radiation intensity may equally be employed.

System 200 can also include a radiation filter 222 deployed in front of both primary sensor 212 and secondary sensor 214. Radiation filter 222 can be configured to reduce the level of incident radiation sufficiently to avoid saturation of the primary sensor even under conditions of direct sunlight. To this end, filter 222 is typically configured to substantially block major sections of the electromagnetic spectrum. In the case that infrared transmission is used, filter 222 can substantially blocks a major part of the infrared portion of the spectrum not required for reception of the reflected signal. Similarly, a major part of the visible spectrum is preferably also substantially blocked.

In this context, "substantial blocking" is used to refer to blocking of at least about 90%, or at least about 95%, of the incident radiation intensity of the blocked wavelengths. Optionally, depending on the sensitivity of the sensors used, filter 222 may be designed to produce an intermediate degree of attenuation, typically between about 40% and about 60% of the intensity, over the first and/or second wavelength ranges. Radiation filters with the required properties also may be produced by generally known techniques including, but not limited to, admixtures of selectively absorptive dyes in an acrylic or polycarbonate base.

In order to provide a substantially reliable measurement of the instantaneous background radiation falling on primary sensor 212, secondary sensor 214 can be deployed adjacent to, and typically as close as possible to, primary sensor 212. As will be described below, system 200 typically employs at least two primary sensors 212. In this case, a corresponding secondary sensor 214 is preferably deployed adjacent to each primary sensor 212, thereby providing an independent indication of the sunlight currently falling on each primary sensor.

Turning now to transmitter 216, this is typically an LED designed to emit a signal of suitable wavelength, preferably within the near infrared range of the spectrum, typically in the range from about 800 to about 1000 nm. Preferred embodiments of the invention employ a plurality of LEDs with diverging lenses to cover a specific zone of interest. Specific geometrical arrangements of both the transmitters and sensors will be discussed below in more detail.

The signal transmitted by transmitter 216 corresponds to a base signal produced by a signal generator 224, modified by compensation module 218 and preferably also by a modulator module 226. Signal generator 224 is preferably configured to generate an underlying pulsed power supply having a duty cycle of less than about 5%, and typically no more than about 2%. In other words, the pulsed power supply is made up of a cycle of pulses of duration such that the total time of the pulses corresponds to no more than about 5% (or about 2%) of the total cycle, the rest of the cycle being unpowered "dead time." By way of example, this could be implemented as a signal generator of base frequency about 38 kHz switched to produce about 100 pulses per second, each of duration about $2 \times 10^4$ seconds corresponding to about 8 peaks of the base frequency. It should be appreciated, however, that the particular choice of base frequency used is not important, and may vary by as much as a few orders of magnitude from the example given. The use of such a low duty cycle helps to avoid overheating of the LEDs.

It should be noted at this point that, for convenience of presentation, the subsequent processing of the underlying pulsed power supply to generate the transmitted signal will be described without extensive reference to the pulsed nature of the power supply. Thus, transmission of the pulsed power supply for 10% of a one second cycle (0.1 second) will be referred to simply as transmission during 10% of a one second cycle. Clearly, the total time over which the LEDs will actually be transmitting is the product of this percentage with the duty cycle percentage.

Modulator module 226 can be configured to modulate the transmission power of the electromagnetic signal cyclically between at least two, and typically three or more, relative power levels each corresponding to a different-sized zone of interest. The highest transmission power produces the highest amplitude reflected signal, leading to detection of an object at a larger distance. The highest relative power level can be generated for less than about 20%, and typically between about 5% and about 15%, of each cycle. The period of cycle used is preferably within an order of magnitude from one second. Typically, the cycle period lies between about 0.2 and about 2 seconds, and most preferably, between about 0.5 and about 1 second. The significance of this choice will become clearer from the description of a preferred implementation of the warning system below.

Figure 13:
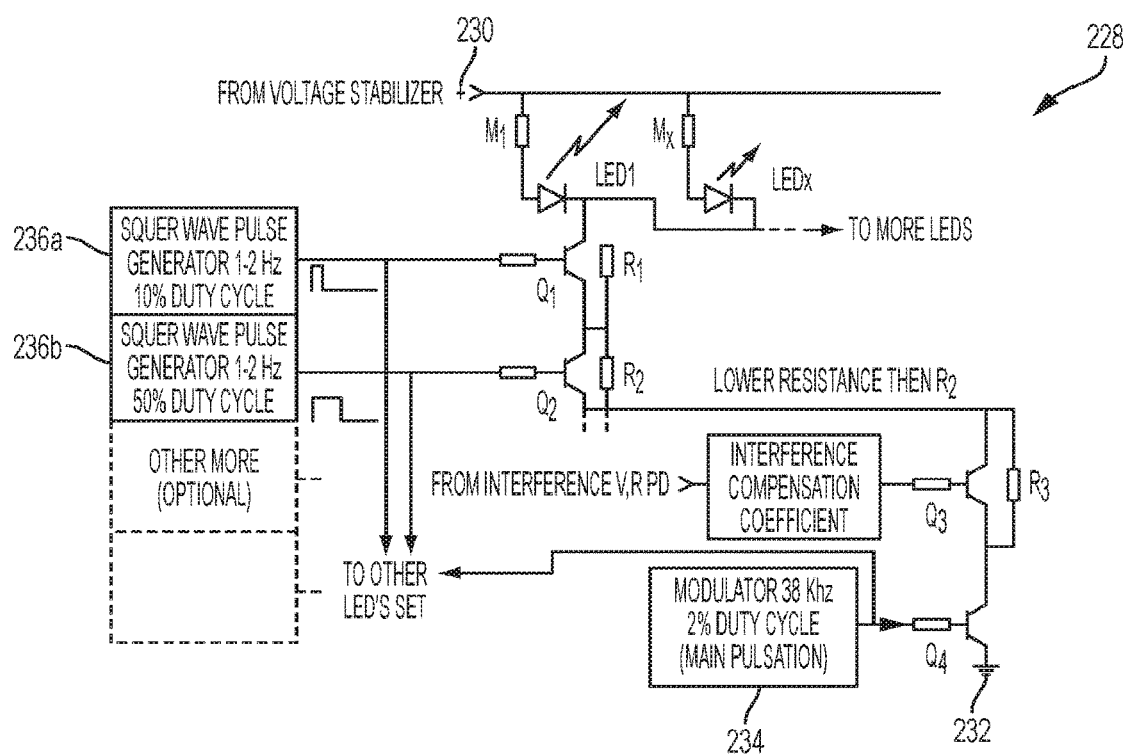
FIG. 13 illustrates a schematic circuit diagram for an example implementation of a modulated transmission subsystem from the system of FIG. 12.

FIG. 13 illustrates a particularly simple and effective direct electronic implementation of the transmission subsystem 228 of system 200 which includes signal generator 224, compensation module 218, modulator module 226, and transmitter(s) 216. As mentioned before, transmitters 216 are implemented as a number of LEDs. Each LED 216 is connected through a dedicated transmission-power modifying resistor M1, Mx etc., between a stabilized voltage source 230 and indirectly to ground 232. Signal generator 224 is implemented as a modulator 234 with an output form as described above connected to operate a transistor switch Q4 which performs rapid switching of the ground connection. When Q4 is closed, the circuit through the LEDs is completed to generate a signal. The intensity of the signal, however, can vary according to the state of a number of additional transistors Q1, Q2 and Q3, each of which is connected in parallel with a corresponding resistor R1, R2 and R3.

Compensation module 218 further can be implemented using transistor Q3 and resistor R3. When the compensation signal indicates high levels of background radiation, such as direct sunlight on the sensors, transistor Q3 effectively shorts across resistor R3 to generate the maximum available intensity transmission from LEDs 216. As the background radiation intensity decreases, the state of Q3 is gradually adjusted to reduce the LEDs intensity until, at low background intensity, resistor R3 reduces the LED intensity to near the lowest value at which the system is operative. In practice, it has been found that under most circumstances, the effect of the background radiation is only very significant under direct sunlight falling on filter 222. As a result, a basic implementation of compensation module may perform simple switching of Q3 between two extreme states. In a more precise implementation, compensation module 218 includes a conversion module, typically implemented as an analog or digital signal processing unit as either a function or look-up table, for converting the compensation signal to an appropriate control voltage for transistor Q3.

Modulator module 226, made up of pulse generators 236a and 236b, transistors Q1 and Q2 and resistors R1 and R2, can provide a low-frequency cyclic modulation superimposed over the power supply variations produced by signal generator 224 and compensation module 218. In this case, two transistor stages are employed to generate three different intensity levels. However, it will be readily apparent that the number of stages may be either increased or decreased according to the number of levels required. Similarly, minor variations would enable more than two levels to be produced by use of a single transistor stage.

In the implementation shown, pulse generators 236a and 236b are synchronous square wave pulse generators operating at a common frequency between about 1 and about 2 Hz. These can differ in the duration of the pulses generated. For example, pulse generator 236a can generate a pulse for 10% of the cycle whereas pulse generator 236b can generate a pulse extending for 50% of the cycle.

Figure 14:
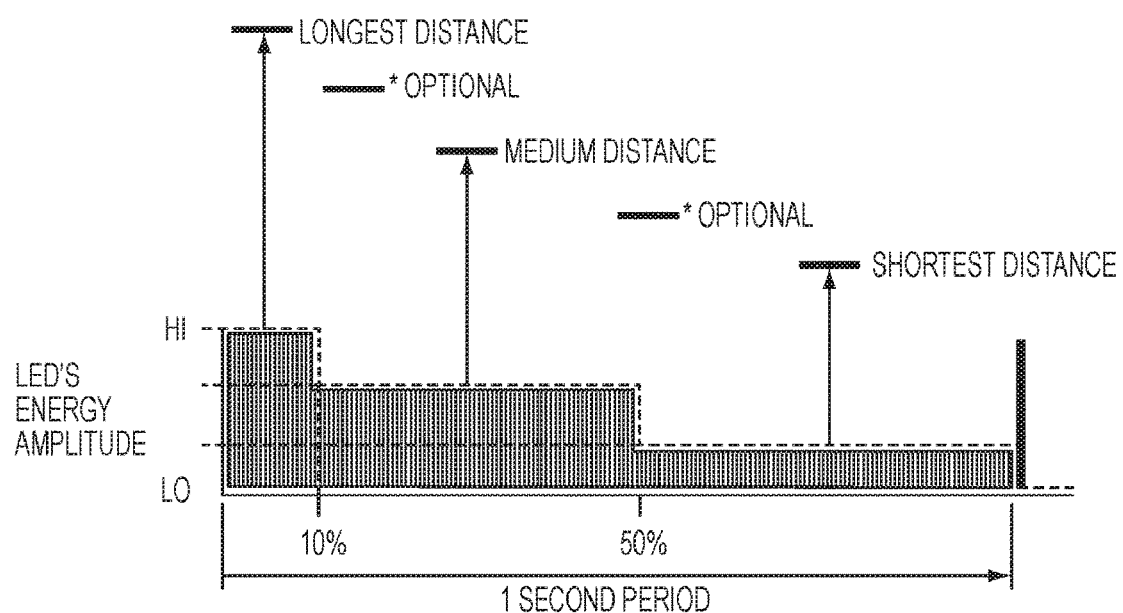
FIG. 14 illustrates a schematic representation of a transmitted signal generated by the modulated transmission subsystem of FIG. 13.

The resulting transmitted signal is shown in FIG. 14. For the first 10% of the cycle, both pulse generators 236a and 236b produce a high output, causing transistors Q1 and Q2 to short across resistors R1 and R2 to generate the full intensity transmission currently allowed by compensation module 218. After the initial 10% pulse, pulse generator 236a goes low, blocking transistor Q1 so that resistor R1 lowers the transmitted intensity to an intermediate relative level. Then, for the second half of the cycle, pulse generator 236b also goes low, blocking transistor Q2 so that resistor R2 further lowers the transmitted intensity to a lowest relative level.

Referring back to FIG. 12, it should be noted that the system shown is readily expandable to any size of transmitter array. The LED array illustrated here may be extended as designated by LEDs, each LED being provided with its own modifying resistor Mx. Additionally, where different arrays of LEDs are to be controlled by independent compensation modules 218, the outputs of signal generator 224 and pulse generators 236a and 236b may be used simultaneously to control additional sets of transistors.

Figure 15:
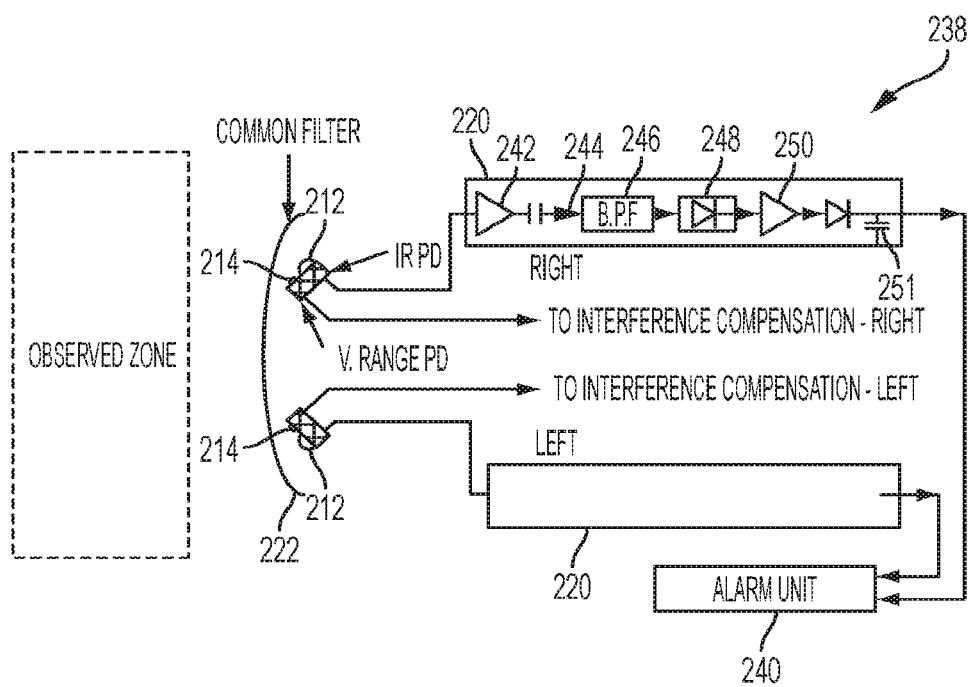
FIG. 15 illustrates a schematic representation of an implementation of a reception sub-system from the system of FIG. 12.

FIG. 15 illustrates a particularly simple and effective direct electronic implementation of the reception sub-system 238 of system 210 which includes sensors 212 and 214, filter 222, processing module 220, and an alarm unit 240. Secondary sensor 214 can be connected to provide its output to compensation module 218, as described. The output of primary sensor 212, on the other hand, is passed to processing module 220 where signal processing is performed to generate an alarm output indicative of the presence of an obstacle within the zone of interest.

Additionally in this implementation, processing module includes an amplifier 242 followed by a capacitor 244 for blocking any DC signal received. The signal then passes through a band pass filter 246 tuned to select only frequencies close to the base frequency of signal generator 224. After rectification at rectifier 248, the signal is passed to a Schmitt trigger 250 which serves to produce an even, noise-free binary output. This output can be supplied through a diode to a grounded capacitor 251 chosen to provide a decay time approximating to the period between pulses of the basic pulsed power supply, thereby "holding" the detected peaks to generate a continuous signal. The resulting output is an on-off DC voltage which generally is sufficiently stable to be fed directly to alarm unit 240.

Alarm unit 240 itself can include an element for generating an audible alarm which may be of any conventional type. Additionally, or alternatively, a visual or tactile warning notification system may be employed. Furthermore, the alarm unit may provide distinguishable warning signals according to which of a number of sensors generated the source signal. Since different sensors correspond to different regions, system 200 can thus provide an indication of within which region or area in which the obstacle lies.

Figure 16:
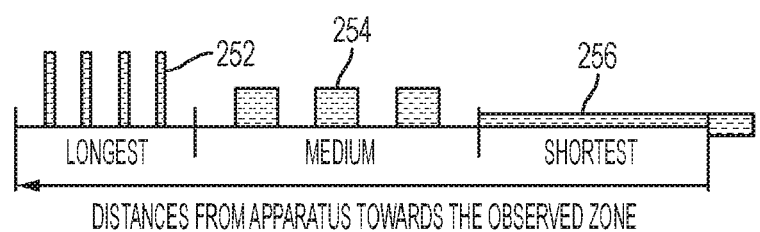
FIG. 16 illustrates a schematic representation of an alarm signal generated by the reception sub-system of FIG. 15 in three different situations.

Referring now additionally to FIG. 16, it is a particular feature of certain embodiments of the present disclosure that the nature and timing of a warning signal generated by system 200 is directly determined by the form of the transmitted signal. Thus, in the example described here, with reference to FIGS. 13-15, the proportion of each one second cycle during which alarm 40 is activated will vary as a direct result of the signal form shown in FIG. 14. When an obstacle is at the boundary of the largest zone of interest, only the highest level signal transmitted during the first 10% of each cycle will produce sufficient reflected intensity to generate an alarm signal. This will result in a series of 0.1 second "blips" 52 at one second intervals. When the obstacle enters the medium size zone of interest, reflection of the medium intensity transmitted signal from 10% to 50% of the cycle will also be sufficiently strong to be detected and to generate an alarm signal. This will result in a more insistent series of ½ second "beeps" 54. Finally, when the obstacle enters the shortest range zone of interest such that even the lowest level transmitted signal produces a detectable reflection, the warning will switch to a continuous tone 256.

It should be noted that, besides the simplicity of such a system, the form of warning notification described can facilitate increased or enhanced recognition. For example, the differences between the three different types of notifications provided are generally immediately and unambiguously identifiable to the human ear, thereby avoiding the problems of misinterpretation which can be common in known warning systems.

It should be noted at this point that the implementations of various components described thus far, as well as variations thereof which will be mentioned below, are provided merely by way of illustration and are by no means exclusive. To illustrate this point, it should be noted that an alternative implementation can readily be achieved by use of a microcomputer together with appropriate software operating under a suitable operating system to replace one or more of signal generator 224, compensation module 218, modulator module 226, and processing module 220. Each module is typically implemented as a separate software module stored within some non-volatile memory device for execution by a CPU. Interfacing with the sensors, transmitters and alarm unit is achieved using conventional analog and/or digital interfaces or samplers as is known in the art.

Turning now to a second set of features relating to deployment of the transmitter and sensor elements, these will be described with reference to FIGS. 17-19. Specifically, system 200 can be configured to warn of the proximity of an obstacle within a zone. In other words, for any given obstacle, a warning should be generated when the obstacle crosses over the virtual line into the zone of interest substantially independent of the position along the line at which it crosses.

In more specific terms, this may be achieved by two types of arrangements which may be used separately or in combination. In the first type, which will be described with reference to FIG. 17, the transmission and sensitivity profiles of transmitter and sensor elements are combined separately to generate profiles approximating to the required zone shape. In the second, described with reference to FIG. 18, the deployment of the transmitters and sensor are coordinated so that a maximum sensitivity direction of the sensor compensates for the minimum in the transmitted intensity pattern.

Figure 17:
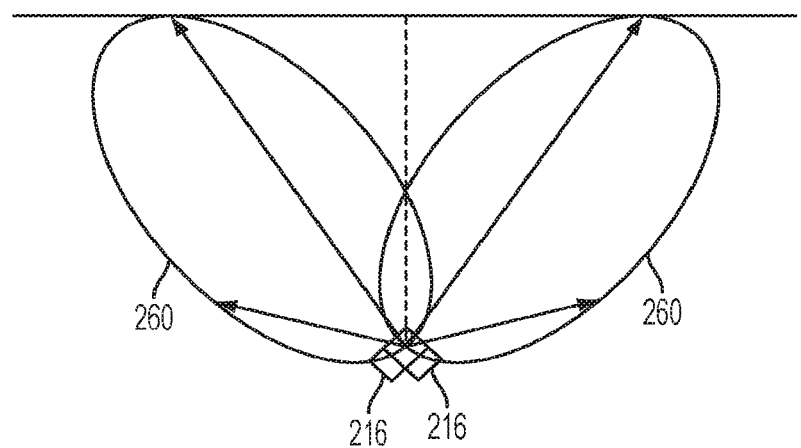
FIG. 17 illustrates a plan view illustrating the superposition of the angular variation of transmitted intensity or reception sensitivity for a pair of transmitters or sensors.

Thus, FIG. 17 shows a pair of transmitters 216 each with a transmission intensity profile 260. Typically, a simple lensed LED exhibits a transmission intensity which decreases as a function of angle from an axial maximum intensity direction. By deploying transmitters 216 with their maximum intensity directions angularly spaced, the degree of overlap between their intensity profiles can be chosen to generate a desired total transmitted intensity at an intermediate position.

By way of example, if the transmission intensity profile of each transmitter decreases to 50% at a given angle, transmitter elements 216 can be deployed with their maximum intensity directions angularly spaced such that their 50% intensity directions are substantially aligned. This generates an approximately uniform total transmission intensity profile between the axial directions of the transmitters. Clearly, if the distance from the transmitters to the required zone boundary decreases between the axial directions, as in the example illustrated, the transmitters can be deployed at a wider angle with, for example, their 40% intensity directions overlapping to generate an 80% intensity at the intermediate position. Conversely, a higher degree of overlap can be used to generate a transmission profile approximating to a longer range boundary of the zone falling between the axial directions.

As already mentioned, this approach can be used both with the transmitter elements and with multiple sensor elements to approximate to a required transmission or sensitivity profile. Sensitivity profiles of typical sensors for use in the present invention are generally similar to those of the transmitters, although the angular spread of a sensor profile is typically larger.

Figure 18:
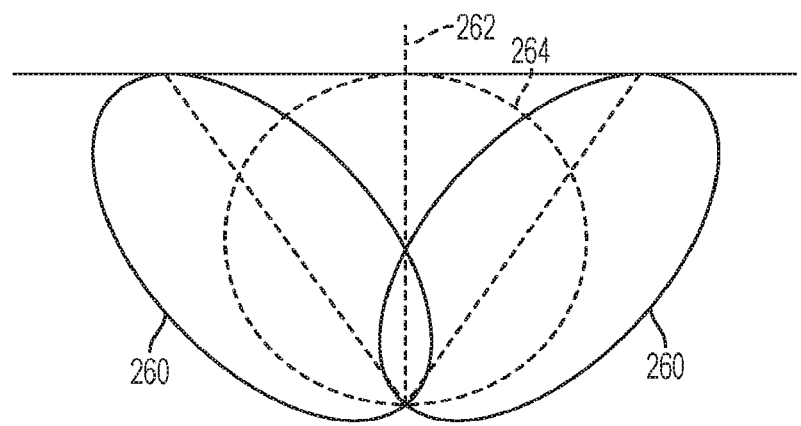
FIG. 18 illustrates a plan view illustrating the superposition of the angular variation of transmitted intensity for a pair of transmitters and reception sensitivity for an interposed sensor.

FIG. 18 shows a pair of transmitters 216 each with a transmission intensity profile 260 which decreases as a function of angle from an axial maximum intensity direction. Transmitters 216 can be deployed with their maximum intensity directions angularly spaced such that a total transmitted intensity assumes a minimum value, typically no more than about 50% of each transmitter's maximum intensity, at an intermediate angular position 262. A sensor 212, with a reception sensitivity profile 264, is aligned with its maximum sensitivity direction aligned substantially with the intermediate angular position 262. This formation ensures that the maximum sensitivity of the sensor is aligned to receive signals reflected from the lowest intensity transmission, whereas the less sensitive sensor directions receive a much stronger reflected signal. The net effect approximates to constant overall sensitivity of the system along the required straight line boundary.

Figure 19:
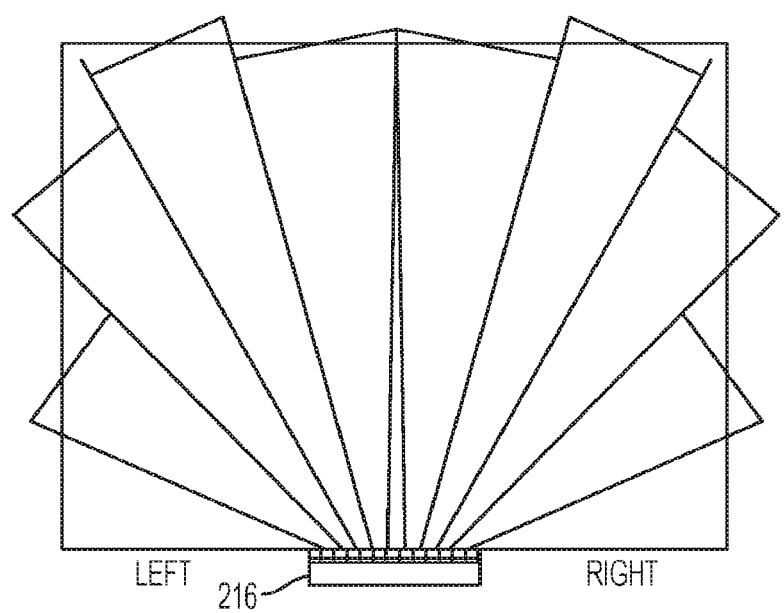
FIG. 19 illustrates a schematic plan view of a pattern of transmitters deployed to provide comprehensive coverage of an approximately rectangular zone.

Finally, with respect to this embodiment, FIG. 19 shows a pattern of transmitters 216 deployed to approximate to a rectangular zone of interest. Besides the considerations already mentioned, it will be noted that the range to be covered by different beams varies considerably both along the far boundary and, in a more pronounced manner, towards the peripheral boundaries. Tailoring of the corresponding beam intensities is achieved by provision of transmission power modifiers associated with each of the transmitter elements, for modifying the effect of the actuating power supply upon the corresponding transmitter element. In the implementation described above, transmission power modifiers correspond to modifying resistors M1, Mx of FIG. 12.

Figure 20:
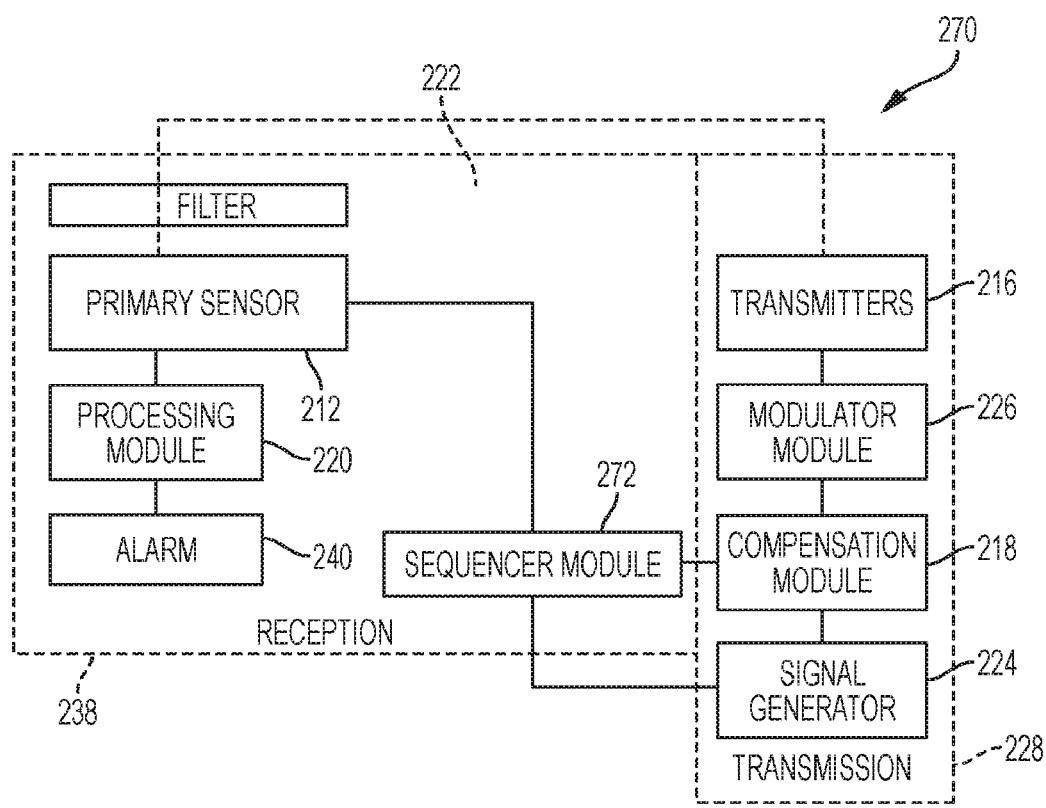
FIG. 20 illustrates a block diagram of an alternative embodiment of a proximity warning system, constructed and operative according to further example teachings of the present disclosure.

Tuning now to FIG. 20, which shows a second embodiment of a proximity warning system, generally designated 270, constructed and operative according to the teachings of the present invention, for warning of the proximity of an obstacle within at least one zone of interest. System 270 is generally similar to system 200, equivalent features being labeled similarly. System 270 is distinguished from system 200 in that the secondary sensor is omitted. Instead, the means for determining the level of background radiation is implemented as a sequencer module 272 which derives the required measurements directly from the output of primary sensor 212.

As described above, the power supply from signal generator 224 preferably has a duty cycle of less than about 5%. As a result, there is a large proportion of dead time during which no transmission occurs. Thus, the output of primary sensor 212 during the dead time intervals is a direct indication of the background intensity level being received by the sensor.

Sequencer module 272 is connected to signal generator 224 so as to be switched synchronously with the pulses of the underlying pulsed power supply. Typically, each pulse initiates a delay circuit in sequencer module 272 which briefly blocks input of a new sensor measurement. Then, once the power supply pulse has finished, sequencer module 272 inputs the current sensor measurement as an indication of the current background radiation level.

In all other respects, the structure and operation of system 270 may be understood by analogy to that of system 200 described above.

The corresponding structures, materials, acts, and equivalents of all means plus function elements in any claims below are intended to include any structure, material, or acts for performing the function in combination with other claim elements as specifically claimed.

It should be noted that the invention includes a first set of features, described with reference to FIGS. 12-16, relating to compensation for background radiation, and a second set of features, described with reference to FIGS. 17-19, relating to geometrical deployment of sensor elements. Each set of features may be used independently in separate systems. However, in a one illustrative embodiment, these features are combined to particular advantage to provide a highly effective and reliable proximity warning system.

The foregoing description generally illustrates and describes various embodiments of the systems and methods of the present disclosure. It will, however, be understood by those skilled in the art that various changes and modifications can be made to the above-discussed methods and systems without departing from the spirit and scope of the invention as disclosed herein, and that it is intended that all matter contained in the above description or shown in the accompanying drawings shall be interpreted as being illustrative, and not to be taken in a limiting sense. Furthermore, the scope of the present disclosure shall be construed to cover various modifications, combinations, additions, alterations, etc., above and to the above-described embodiments, which shall be considered to be within the scope of the present invention. Accordingly, various features and characteristics of the systems and methods as discussed herein may be selectively interchanged and applied to other illustrated and non-illustrated embodiments of the invention, and numerous variations, modifications, and additions further can be made thereto without departing from the spirit and scope of the present invention as set forth in the appended claims.

What is claimed is:

1. A system for identifying and mapping movements of personnel within a facility, comprising:
   a plurality of badges each assigned to selected individuals of the personnel in the facility, each badge comprising one or more transmitters configured to transmit one or more signals including signature information identifying each badge from which the one or more signals are transmitted;

a plurality of dispensers positioned at selected locations about the facility, each dispenser of the plurality of dispensers including a plurality of receivers disposed therealong and configured to receive the one or more signals transmitted by each badge, wherein each receiver of the plurality of receivers is positioned or configured to receive the one or more signals within a prescribed area or zone around the dispenser associated with each receiver; and a processor in communication with the plurality of dispensers and configured to map movements of the personnel throughout the facility based on information received from the plurality of receivers and the signature information included in the one or more signals, wherein when the one or more signals transmitted by the badges are received by at least one receiver of the plurality of receivers, the processor determines and records that the individuals assigned to the one or more badges entered the prescribed area or zone associated with the at least one receiver.

2. The system according to claim 1, wherein one or more of the plurality of dispensers includes a sanitation device.

3. The system according to claim 2, wherein one or more receivers of the plurality of receivers are configured to detect use of the sanitation device and transmit the information to the processor including an identity of individuals of the personnel carrying the badge based on the signature information and indicating whether the identified individuals of the personnel used the sanitation device.

4. The system according to claim 1,
wherein one or more receivers of the plurality of receivers are configured to transmit information indicating a proximity, range, or distance between the receivers and the one or more badges detected by the receivers to the processor.

5. The system according to claim 4, further comprising:
a database storing data including information on medical patients checked into the facility, wherein the processor is in communication with the database and is configured to cross-reference the information on the medical patients stored in the database and the information including the proximity, range, or distance between the one or more receivers and the one or more badges detected by the receivers, and the signature information identifying each badge, to alert individuals carrying badges detected by the receiver to take a particular action or to allow or restrict access to the individuals to different areas of the facility.

6. The system according to claim 1, wherein the transmitters of each badge are configured to initiate transmission of their one or more signals in response to a transmission received from one or more receivers of the plurality of receivers, when the badges are within a prescribed proximity, distance, range, or zone of the one or more receivers.

7. The system of claim 1, wherein the one or more transmitters of each badge are configured to transmit a plurality of signals each containing at least one identifying code identifying each signal.

8. The system of claim 1, wherein each signal of the plurality of signals is transmitted at a predetermined distance from each badge or at different signal strengths.

9. The system of claim 8, wherein the processor determines a plurality of positions or movements of each badge in relation to one or more of the plurality of receivers, based on differing signals of the plurality of signals received at the one or more receivers from each badge.

10. The system of claim 9, wherein the plurality of signals includes at least five signals each transmitted at a predetermined distance, and wherein a variation between the predetermined distance at which each of the plurality of signals is transmitted is between about 5 in. to about 1 ft.

11. The system of claim 1, wherein each dispenser of the plurality of dispensers includes a housing and wherein at least one of the plurality of receivers is disposed on a first side of the housing and at least one of the plurality of receivers is disposed on a second side of the housing.

12. The system of claim 1, wherein each dispenser of the plurality of dispensers includes a side bar with the plurality of receivers arranged therealong.

13. A system for tracking, locating, and mapping movements of medical workers in a medical facility, comprising:
a plurality of badges carried by one or more selected medical workers, each badge comprising at least one transmitter configured to transmit one or more signals, each signal of the one or more signals including signature information identifying the badges carried by each of the selected medical workers; and a plurality of dispensers positioned adjacent a patient treatment area of the medical facility, each of the dispensers including a plurality of receivers being configured to transmit an activation signal to cause badges in a desired proximity thereto to transmit their one or more signals, and positioned to receive the one or more signals within a prescribed zone or area associated with each receiver; and a processor in communication with the plurality of receivers and configured to create records of the one or more signals based on information received from the plurality of receivers, including the identity of each of the badges detected as coming within the prescribed zones or areas associated with one or more receivers of the plurality of receivers.

14. The system according to claim 13, wherein each badge further includes a badge receiver configured to receive the activation signal as each badge moves within the desired proximity to activate the badge and initiate the transmission of the one or more signals.

15. The system of claim 13, wherein one or more of the dispensers includes a sanitation device including one or more notification devices that notify the selected medical worker to perform a sanitation action in response to one or more of the receivers receiving the one or more signals transmitted from the badges.

16. The system of claim 13, wherein the one or more transmitters of each badge are configured to transmit a plurality of signals each containing at least one identifying code identifying each signal.

17. The system of claim 16, wherein each signal of the plurality of signals is transmitted at a predetermined distance from each badge or at different signal strengths.

18. The system of claim 17, wherein the processor determines a plurality of positions or movements of each badge in relation to one or more of the plurality of receivers, based on differing signals of the plurality of signals received at the one or more receivers from each badge.

19. The system of claim 18, wherein the plurality of signals includes at least five signals each transmitted at a predetermined distance, and wherein a variation between the predetermined distance at which each of the plurality of signals is transmitted is between about 5 in. to about 1 ft.

20. The system of claim 13, wherein each dispenser of the plurality of dispensers includes a housing and wherein at least one of the plurality of receivers is disposed on a first side of the housing and at least one of the plurality of receivers is disposed on a second side of the housing.

21. The system of claim 13, wherein each dispenser of the plurality of dispensers includes a side bar with the plurality of receivers arranged therealong.

* * * * *